US010143718B2

(12) United States Patent
van der Vliet et al.

(10) Patent No.: US 10,143,718 B2
(45) Date of Patent: Dec. 4, 2018

(54) COVALENT INHIBITORS OF DUAL OXIDASE 1 (DUOX 1)

(71) Applicant: The University of Vermont and State Agricultural College, Burlington, VT (US)

(72) Inventors: Albert van der Vliet, Essex, VT (US); David Earl Heppner, Burlington, VT (US); Karamatullah Danyal, South Burlington, VT (US)

(73) Assignee: The University of Vermont and State Agricultural College, Burlington, VT (US)

( * ) Notice: Subject to any disclaimer, the term of this patent is extended or adjusted under 35 U.S.C. 154(b) by 0 days.

(21) Appl. No.: 15/299,848

(22) Filed: Oct. 21, 2016

(65) Prior Publication Data

US 2017/0128517 A1 May 11, 2017

Related U.S. Application Data

(60) Provisional application No. 62/245,114, filed on Oct. 22, 2015.

(51) Int. Cl.
*A61K 38/03* (2006.01)
*A61K 9/00* (2006.01)

(52) U.S. Cl.
CPC ............ *A61K 38/03* (2013.01); *A61K 9/0073* (2013.01)

(58) Field of Classification Search
None
See application file for complete search history.

(56) References Cited

PUBLICATIONS

Danyal et al., Acrolein and thiol-reactive electrophiles suppress allergen-induced innate airway epithelial responses by inhibition of DUOX1 and EGFR. Am J Physiol Lung Cell Mol Physiol. Nov. 1, 2016;311(5):L913-L923. doi: 10.1152/ajplung.00276.2016. Epub Sep. 9, 2016.

Hristova et al., Airway epithelial dual oxidase 1 mediates allergen-induced IL-33 secretion and activation of type 2 immune responses. J Allergy Clin Immunol. May 2016;137(5):1545-1556.e11. doi: 10.1016/j.jaci.2015.10.003. Epub Nov. 17, 2015.

*Primary Examiner* — Lianko G Garyu
(74) *Attorney, Agent, or Firm* — Wolf, Greenfield & Sacks, P.C.

(57) ABSTRACT

The present invention generally relates to inhibitors of DUOX1. In some aspects, an inhibitor may be applied to a subject having or being at risk for asthma or other conditions. The inhibitor may be applied by various techniques, such as pulmonary or topical delivery. In some embodiments, the inhibitor may include a peptide or other moiety having a reactive electrophile. The reactive electrophile can target cysteine or other residues within DUOX1 to inhibit its activity, e.g., by covalently binding to the residue. Other non-limiting examples of suitable inhibitors include hydroxynonenal, curcumin, sulforaphane, cinnamaldehyde, dimethyl fumarate, or phenyl vinyl sulfonate. Other aspects of the invention are generally directed to methods of making or using such inhibitors, kits involving such inhibitors, devices or formulations containing such inhibitors, or the like.

20 Claims, 5 Drawing Sheets

Specification includes a Sequence Listing.

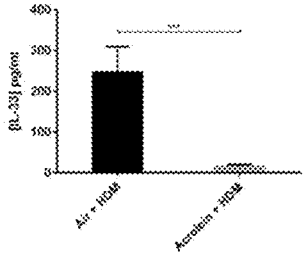
Fig. 1A
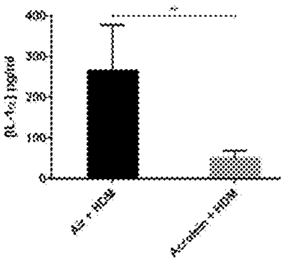
Fig. 1B
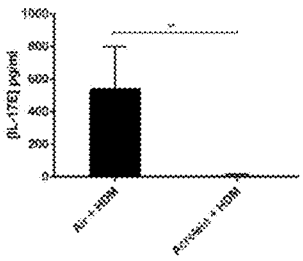
Fig. 1C
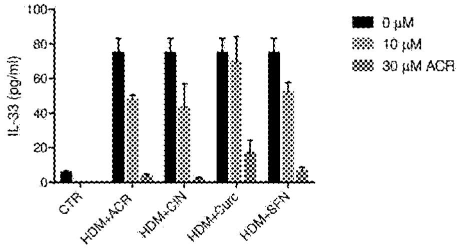
Fig. 2
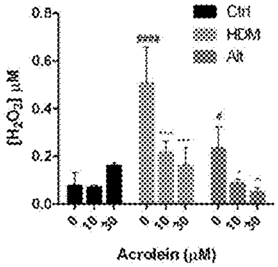
Fig. 3
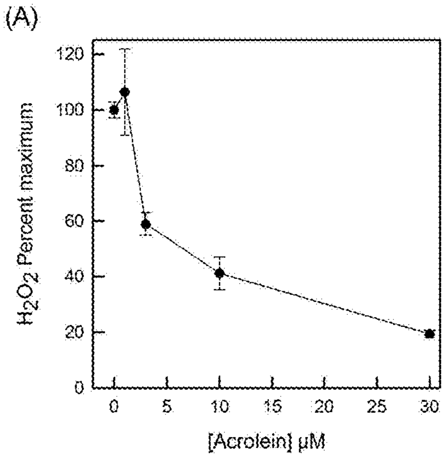
Fig. 4A
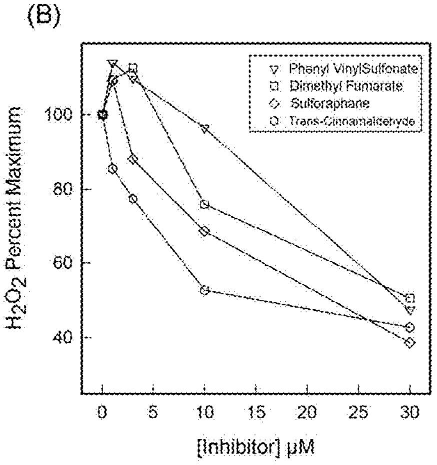
Fig. 4B
(C)
| Concentration µM | Percent inhibition of $H_2O_2$ production | | |
|---|---|---|---|
| | Acrolein | Sulforaphane | Trans-cinnamaldehyde |
| 10 | 59 ± 6 | 74 ± 3 | 45 ± 4 |
| 30 | 81 ± 2 | 92 ± 8 | 73 ± 17 |
Fig. 4C Fig. 7A
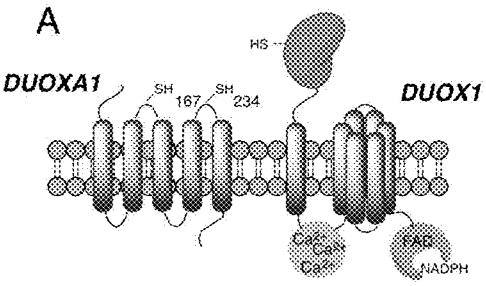
Fig. 7B
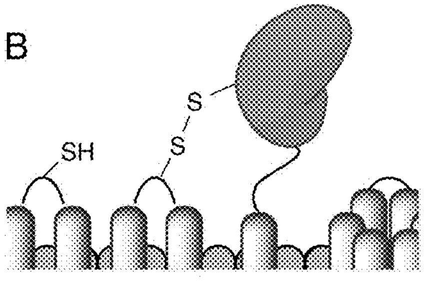
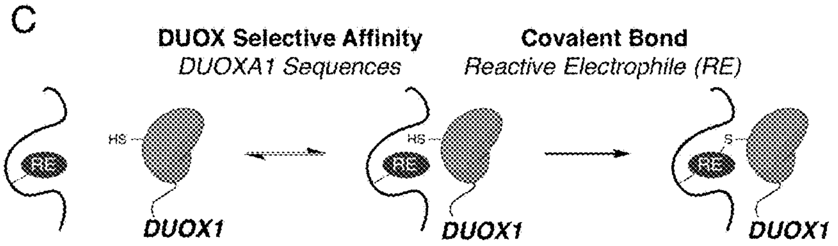
Fig. 7C
Fig. 8A
A
```
DUOXA1  162   TPRSPCGLYRQ   172 SEQ ID NO: 1
              TP SPCGLY Q
DUOXA2  162   TPSSPCGLYHQ   172 SEQ ID NO: 2

DUOXA1  230   LTSP-CPLHLG   240 SEQ ID NO: 3
                + P CPL LG
DUOXA2  229   SSVPLCPLRLG   239 SEQ ID NO: 4
```
Fig. 8B
B
SEQ ID NO: 1
$T^{162}PRSPCGLYRQ^{172}$
$S^{292}LTSPCPLHLG^{240}$
SEQ ID NO: 5
C
XSPCXLX
SEQ ID NO: 6
Fig. 8C

Fig. 11

```
   1 mgfclalawt llvgawtplg aqnpiswevq rfdgwynnlm ehrwgskgsr lqrlvpasya
  61 dgvyqplgep hlpnprdlsn tisrgpagla slrnrtvlgv ffgyhvlsdl vsvetpgcpa
 121 eflnirippg dpmfdpdqrg dvvlpfqrsr wdpetgrsps nprdpanqvt gwldgsaiyg
 181 sshswsdalr sfsrgqlasg pdpafprdsq npllmwaapd patgqngprg lyafgaergn
 241 repflqalgl lwfryhnlwa qrlarqhpdw edeelfqhar krviatyqni avyewlpsfl
 301 qktlpeytgy rpfldpsiss efvaaseqfl stmvppgvym rnaschfqgv inrnssvsra
 361 lrvcnsywsr ehpslqsaed vdalllgmas qiaeredhvl vedvrdfwpg plkfsrtdhl
 421 asclqrgrdl glpsytkara alglspitrw qdinpalsrs ndtvleataa lynqdlswle
 481 llpggllesh rdpgplfsti vleqfvrlrd gdrywfentr nglfskkeie eirnttlqdv
 541 lvavinidps alqpnvfvwh kgdpcpqprq lsteglpara psvvrdyfeg sgfgfgvtig
 601 tlccfplvsl lsawivarlr mrnfkrlqgq drqsivsekl vggmealewq ghkepcrpvl
 661 vylqpgqirv vdgrltvlrt iqlqppqkvn fvlssnrgrr tlllkipkey dlvllfnlee
 721 erqalvenlr galkesglsi qewelreqel mraavtreqr rhlletffrh lfsqvldinq
 781 adagtlplds sqkvrealtc elsraefaes lglkpqdmfv esmfsladkd gngylsfref
 841 ldilvvfmkg speeksrlmf rmydfdgngl iskdefirml rsfieisnnc lskaqlaevv
 901 esmfresgfq dkeeltwedf hfmlrdhnse lrftqlcvkg vevpevikdl crrasyisqd
 961 micpsprvsa rcsrsdiete ltpqrlqcpm dtdppqeirr rfgkkvtsfq pllfteahre
1021 kfqrsclhqt vqqfkrfien yrrhigcvav fyaiagglfl erayyyafaa hhtgitdttr
1081 vgiilsrgta asisfmfsyi lltmcrnlit flretflnry vpfdaavdfh rliastaivl
1141 tvlhsvghvv nvylfsispl svlsclfpgl fhddgsefpq kyywwffqtv pgltgvvlll
1201 ilaimyvfas hhfrrrsfrg fwlthhlyil lyvlliihgs faliqlprfh ifflvpaiiy
1261 ggdklvslsr kkveisvvka ellpsgvthl rfqrpqgfey ksgqwvriac lalgtteyhp
1321 ftltsaphed tlslhiraag pwttrlreiy saptgdrcar ypklyldgpf geghqewhkf
1381 evsvlvgggi gvtpfasilk dlvfkssvsc qvfckkiyfi wvtrtqrqfe wladiireve
1441 endhqdlvsv hiyitqlaek fdlrttmlyi cerhfqkvln rslftglrsi thfgrppfep
1501 ffnslqevhp qvrkigvfsc gppgmtknve kacqlinrqd rthfshhyen f
```

SEQ ID NO: 7

SEQUENCE LISTING

```
<160> NUMBER OF SEQ ID NOS: 35

<210> SEQ ID NO 1
<211> LENGTH: 11
<212> TYPE: PRT
<213> ORGANISM: Homo sapiens

<400> SEQUENCE: 1
```

```
Thr Pro Arg Ser Pro Cys Gly Leu Tyr Arg Gln
1               5                   10


<210> SEQ ID NO 2
<211> LENGTH: 11
<212> TYPE: PRT
<213> ORGANISM: Homo sapiens

<400> SEQUENCE: 2

Thr Pro Ser Ser Pro Cys Gly Leu Tyr His Gln
1               5                   10


<210> SEQ ID NO 3
<211> LENGTH: 10
<212> TYPE: PRT
<213> ORGANISM: Homo sapiens

<400> SEQUENCE: 3

Leu Thr Ser Pro Cys Pro Leu His Leu Gly
1               5                   10


<210> SEQ ID NO 4
<211> LENGTH: 11
<212> TYPE: PRT
<213> ORGANISM: Homo sapiens

<400> SEQUENCE: 4

Ser Ser Val Pro Leu Cys Pro Leu Arg Leu Gly
1               5                   10


<210> SEQ ID NO 5
<211> LENGTH: 11
<212> TYPE: PRT
<213> ORGANISM: Homo sapiens

<400> SEQUENCE: 5

Ser Leu Thr Ser Pro Cys Pro Leu His Leu Gly
1               5                   10


<210> SEQ ID NO 6
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 6

Xaa Ser Pro Cys Xaa Leu Xaa
1               5


<210> SEQ ID NO 7
<211> LENGTH: 1551
<212> TYPE: PRT
<213> ORGANISM: Homo sapiens
```

<400> SEQUENCE: 7

```
Met Gly Phe Cys Leu Ala Leu Ala Trp Thr Leu Leu Val Gly Ala Trp
1               5                   10                  15

Thr Pro Leu Gly Ala Gln Asn Pro Ile Ser Trp Glu Val Gln Arg Phe
            20                  25                  30

Asp Gly Trp Tyr Asn Asn Leu Met Glu His Arg Trp Gly Ser Lys Gly
        35                  40                  45

Ser Arg Leu Gln Arg Leu Val Pro Ala Ser Tyr Ala Asp Gly Val Tyr
    50                  55                  60

Gln Pro Leu Gly Glu Pro His Leu Pro Asn Pro Arg Asp Leu Ser Asn
65                  70                  75                  80

Thr Ile Ser Arg Gly Pro Ala Gly Leu Ala Ser Leu Arg Asn Arg Thr
                85                  90                  95

Val Leu Gly Val Phe Phe Gly Tyr His Val Leu Ser Asp Leu Val Ser
            100                 105                 110

Val Glu Thr Pro Gly Cys Pro Ala Glu Phe Leu Asn Ile Arg Ile Pro
        115                 120                 125

Pro Gly Asp Pro Met Phe Asp Pro Asp Gln Arg Gly Asp Val Val Leu
    130                 135                 140

Pro Phe Gln Arg Ser Arg Trp Asp Pro Glu Thr Gly Arg Ser Pro Ser
145                 150                 155                 160

Asn Pro Arg Asp Pro Ala Asn Gln Val Thr Gly Trp Leu Asp Gly Ser
                165                 170                 175

Ala Ile Tyr Gly Ser Ser His Ser Trp Ser Asp Ala Leu Arg Ser Phe
            180                 185                 190

Ser Arg Gly Gln Leu Ala Ser Gly Pro Asp Pro Ala Phe Pro Arg Asp
        195                 200                 205

Ser Gln Asn Pro Leu Leu Met Trp Ala Ala Pro Asp Pro Ala Thr Gly
    210                 215                 220

Gln Asn Gly Pro Arg Gly Leu Tyr Ala Phe Gly Ala Glu Arg Gly Asn
225                 230                 235                 240

Arg Glu Pro Phe Leu Gln Ala Leu Gly Leu Leu Trp Phe Arg Tyr His
                245                 250                 255

Asn Leu Trp Ala Gln Arg Leu Ala Arg Gln His Pro Asp Trp Glu Asp
            260                 265                 270

Glu Glu Leu Phe Gln His Ala Arg Lys Arg Val Ile Ala Thr Tyr Gln
        275                 280                 285

Asn Ile Ala Val Tyr Glu Trp Leu Pro Ser Phe Leu Gln Lys Thr Leu
    290                 295                 300

Pro Glu Tyr Thr Gly Tyr Arg Pro Phe Leu Asp Pro Ser Ile Ser Ser
305                 310                 315                 320

Glu Phe Val Ala Ala Ser Glu Gln Phe Leu Ser Thr Met Val Pro Pro
                325                 330                 335

Gly Val Tyr Met Arg Asn Ala Ser Cys His Phe Gln Gly Val Ile Asn
            340                 345                 350

Arg Asn Ser Ser Val Ser Arg Ala Leu Arg Val Cys Asn Ser Tyr Trp
        355                 360                 365

Ser Arg Glu His Pro Ser Leu Gln Ser Ala Glu Asp Val Asp Ala Leu
    370                 375                 380

Leu Leu Gly Met Ala Ser Gln Ile Ala Glu Arg Glu Asp His Val Leu
385                 390                 395                 400

Val Glu Asp Val Arg Asp Phe Trp Pro Gly Pro Leu Lys Phe Ser Arg
                405                 410                 415
```

-continued

```
Thr Asp His Leu Ala Ser Cys Leu Gln Arg Gly Arg Asp Leu Gly Leu
            420                 425                 430

Pro Ser Tyr Thr Lys Ala Arg Ala Ala Leu Gly Leu Ser Pro Ile Thr
        435                 440                 445

Arg Trp Gln Asp Ile Asn Pro Ala Leu Ser Arg Ser Asn Asp Thr Val
    450                 455                 460

Leu Glu Ala Thr Ala Ala Leu Tyr Asn Gln Asp Leu Ser Trp Leu Glu
465                 470                 475                 480

Leu Leu Pro Gly Gly Leu Leu Glu Ser His Arg Asp Pro Gly Pro Leu
                485                 490                 495

Phe Ser Thr Ile Val Leu Glu Gln Phe Val Arg Leu Arg Asp Gly Asp
            500                 505                 510

Arg Tyr Trp Phe Glu Asn Thr Arg Asn Gly Leu Phe Ser Lys Lys Glu
        515                 520                 525

Ile Glu Glu Ile Arg Asn Thr Thr Leu Gln Asp Val Leu Val Ala Val
    530                 535                 540

Ile Asn Ile Asp Pro Ser Ala Leu Gln Pro Asn Val Phe Val Trp His
545                 550                 555                 560

Lys Gly Asp Pro Cys Pro Gln Pro Arg Gln Leu Ser Thr Glu Gly Leu
                565                 570                 575

Pro Ala Arg Ala Pro Ser Val Val Arg Asp Tyr Phe Glu Gly Ser Gly
            580                 585                 590

Phe Gly Phe Gly Val Thr Ile Gly Thr Leu Cys Cys Phe Pro Leu Val
        595                 600                 605

Ser Leu Leu Ser Ala Trp Ile Val Ala Arg Leu Arg Met Arg Asn Phe
    610                 615                 620

Lys Arg Leu Gln Gly Gln Asp Arg Gln Ser Ile Val Ser Glu Lys Leu
625                 630                 635                 640

Val Gly Gly Met Glu Ala Leu Glu Trp Gln Gly His Lys Glu Pro Cys
                645                 650                 655

Arg Pro Val Leu Val Tyr Leu Gln Pro Gly Gln Ile Arg Val Val Asp
            660                 665                 670

Gly Arg Leu Thr Val Leu Arg Thr Ile Gln Leu Gln Pro Pro Gln Lys
        675                 680                 685

Val Asn Phe Val Leu Ser Ser Asn Arg Gly Arg Arg Thr Leu Leu Leu
    690                 695                 700

Lys Ile Pro Lys Glu Tyr Asp Leu Val Leu Leu Phe Asn Leu Glu Glu
705                 710                 715                 720

Glu Arg Gln Ala Leu Val Glu Asn Leu Arg Gly Ala Leu Lys Glu Ser
                725                 730                 735

Gly Leu Ser Ile Gln Glu Trp Glu Leu Arg Glu Gln Glu Leu Met Arg
            740                 745                 750

Ala Ala Val Thr Arg Glu Gln Arg Arg His Leu Leu Glu Thr Phe Phe
        755                 760                 765

Arg His Leu Phe Ser Gln Val Leu Asp Ile Asn Gln Ala Asp Ala Gly
    770                 775                 780

Thr Leu Pro Leu Asp Ser Ser Gln Lys Val Arg Glu Ala Leu Thr Cys
785                 790                 795                 800

Glu Leu Ser Arg Ala Glu Phe Ala Glu Ser Leu Gly Leu Lys Pro Gln
                805                 810                 815

Asp Met Phe Val Glu Ser Met Phe Ser Leu Ala Asp Lys Asp Gly Asn
            820                 825                 830
```

-continued

```
Gly Tyr Leu Ser Phe Arg Glu Phe Leu Asp Ile Leu Val Val Phe Met
        835                 840                 845

Lys Gly Ser Pro Glu Glu Lys Ser Arg Leu Met Phe Arg Met Tyr Asp
    850                 855                 860

Phe Asp Gly Asn Gly Leu Ile Ser Lys Asp Glu Phe Ile Arg Met Leu
865                 870                 875                 880

Arg Ser Phe Ile Glu Ile Ser Asn Asn Cys Leu Ser Lys Ala Gln Leu
                885                 890                 895

Ala Glu Val Val Glu Ser Met Phe Arg Glu Ser Gly Phe Gln Asp Lys
            900                 905                 910

Glu Glu Leu Thr Trp Glu Asp Phe His Phe Met Leu Arg Asp His Asn
        915                 920                 925

Ser Glu Leu Arg Phe Thr Gln Leu Cys Val Lys Gly Val Glu Val Pro
    930                 935                 940

Glu Val Ile Lys Asp Leu Cys Arg Arg Ala Ser Tyr Ile Ser Gln Asp
945                 950                 955                 960

Met Ile Cys Pro Ser Pro Arg Val Ser Ala Arg Cys Ser Arg Ser Asp
                965                 970                 975

Ile Glu Thr Glu Leu Thr Pro Gln Arg Leu Gln Cys Pro Met Asp Thr
            980                 985                 990

Asp Pro Pro Gln Glu Ile Arg Arg  Arg Phe Gly Lys Lys  Val Thr Ser
        995                 1000                1005

Phe Gln  Pro Leu Leu Phe Thr  Glu Ala His Arg Glu  Lys Phe Gln
    1010                1015                1020

Arg Ser  Cys Leu His Gln Thr  Val Gln Gln Phe Lys  Arg Phe Ile
    1025                1030                1035

Glu Asn  Tyr Arg Arg His Ile  Gly Cys Val Ala Val  Phe Tyr Ala
    1040                1045                1050

Ile Ala  Gly Gly Leu Phe Leu  Glu Arg Ala Tyr Tyr  Tyr Ala Phe
    1055                1060                1065

Ala Ala  His His Thr Gly Ile  Thr Asp Thr Thr Arg  Val Gly Ile
    1070                1075                1080

Ile Leu  Ser Arg Gly Thr Ala  Ala Ser Ile Ser Phe  Met Phe Ser
    1085                1090                1095

Tyr Ile  Leu Leu Thr Met Cys  Arg Asn Leu Ile Thr  Phe Leu Arg
    1100                1105                1110

Glu Thr  Phe Leu Asn Arg Tyr  Val Pro Phe Asp Ala  Ala Val Asp
    1115                1120                1125

Phe His  Arg Leu Ile Ala Ser  Thr Ala Ile Val Leu  Thr Val Leu
    1130                1135                1140

His Ser  Val Gly His Val Val  Asn Val Tyr Leu Phe  Ser Ile Ser
    1145                1150                1155

Pro Leu  Ser Val Leu Ser Cys  Leu Phe Pro Gly Leu  Phe His Asp
    1160                1165                1170

Asp Gly  Ser Glu Phe Pro Gln  Lys Tyr Tyr Trp Trp  Phe Phe Gln
    1175                1180                1185

Thr Val  Pro Gly Leu Thr Gly  Val Val Leu Leu Leu  Ile Leu Ala
    1190                1195                1200

Ile Met  Tyr Val Phe Ala Ser  His His Phe Arg Arg  Arg Ser Phe
    1205                1210                1215

Arg Gly  Phe Trp Leu Thr His  His Leu Tyr Ile Leu  Leu Tyr Val
    1220                1225                1230

Leu Leu  Ile Ile His Gly Ser  Phe Ala Leu Ile Gln  Leu Pro Arg
```

-continued

```
    1235                1240                1245

Phe His  Ile Phe Phe Leu Val  Pro Ala Ile Ile Tyr  Gly Gly Asp
    1250                1255                1260

Lys Leu  Val Ser Leu Ser Arg  Lys Lys Val Glu Ile  Ser Val Val
    1265                1270                1275

Lys Ala  Glu Leu Leu Pro Ser  Gly Val Thr His Leu  Arg Phe Gln
    1280                1285                1290

Arg Pro  Gln Gly Phe Glu Tyr  Lys Ser Gly Gln Trp  Val Arg Ile
    1295                1300                1305

Ala Cys  Leu Ala Leu Gly Thr  Thr Glu Tyr His Pro  Phe Thr Leu
    1310                1315                1320

Thr Ser  Ala Pro His Glu Asp  Thr Leu Ser Leu His  Ile Arg Ala
    1325                1330                1335

Ala Gly  Pro Trp Thr Thr Arg  Leu Arg Glu Ile Tyr  Ser Ala Pro
    1340                1345                1350

Thr Gly  Asp Arg Cys Ala Arg  Tyr Pro Lys Leu Tyr  Leu Asp Gly
    1355                1360                1365

Pro Phe  Gly Glu Gly His Gln  Glu Trp His Lys Phe  Glu Val Ser
    1370                1375                1380

Val Leu  Val Gly Gly Gly Ile  Gly Val Thr Pro Phe  Ala Ser Ile
    1385                1390                1395

Leu Lys  Asp Leu Val Phe Lys  Ser Ser Val Ser Cys  Gln Val Phe
    1400                1405                1410

Cys Lys  Lys Ile Tyr Phe Ile  Trp Val Thr Arg Thr  Gln Arg Gln
    1415                1420                1425

Phe Glu  Trp Leu Ala Asp Ile  Ile Arg Glu Val Glu  Glu Asn Asp
    1430                1435                1440

His Gln  Asp Leu Val Ser Val  His Ile Tyr Ile Thr  Gln Leu Ala
    1445                1450                1455

Glu Lys  Phe Asp Leu Arg Thr  Thr Met Leu Tyr Ile  Cys Glu Arg
    1460                1465                1470

His Phe  Gln Lys Val Leu Asn  Arg Ser Leu Phe Thr  Gly Leu Arg
    1475                1480                1485

Ser Ile  Thr His Phe Gly Arg  Pro Pro Phe Glu Pro  Phe Phe Asn
    1490                1495                1500

Ser Leu  Gln Glu Val His Pro  Gln Val Arg Lys Ile  Gly Val Phe
    1505                1510                1515

Ser Cys  Gly Pro Pro Gly Met  Thr Lys Asn Val Glu  Lys Ala Cys
    1520                1525                1530

Gln Leu  Ile Asn Arg Gln Asp  Arg Thr His Phe Ser  His His Tyr
    1535                1540                1545

Glu Asn  Phe
    1550
```

<210> SEQ ID NO 8
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa is a reactive electrophile
<220> FEATURE:
<221> NAME/KEY: misc_feature
<222> LOCATION: (4)..(4)

```
<223> OTHER INFORMATION: Xaa can be Gly or Pro

<400> SEQUENCE: 8

Ser Pro Xaa Xaa Leu
1               5


<210> SEQ ID NO 9
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be Phe or Thr
<220> FEATURE:
<221> NAME/KEY: misc_feature
<222> LOCATION: (2)..(2)
<223> OTHER INFORMATION: Xaa can be Thr or Ser
<220> FEATURE:
<221> NAME/KEY: misc_feature
<222> LOCATION: (3)..(3)
<223> OTHER INFORMATION: Xaa can be Pro or Leu
<220> FEATURE:
<221> NAME/KEY: misc_feature
<222> LOCATION: (4)..(4)
<223> OTHER INFORMATION: Xaa can be Arg or Thr
<220> FEATURE:
<221> NAME/KEY: misc_feature
<222> LOCATION: (7)..(7)
<223> OTHER INFORMATION: Xaa is a reactive electrophile
<220> FEATURE:
<221> NAME/KEY: misc_feature
<222> LOCATION: (8)..(8)
<223> OTHER INFORMATION: Xaa can be Gly or Pro
<220> FEATURE:
<221> NAME/KEY: misc_feature
<222> LOCATION: (10)..(10)
<223> OTHER INFORMATION: Xaa can be Tyr or His
<220> FEATURE:
<221> NAME/KEY: misc_feature
<222> LOCATION: (11)..(11)
<223> OTHER INFORMATION: Xaa can be Arg or Leu
<220> FEATURE:
<221> NAME/KEY: misc_feature
<222> LOCATION: (12)..(12)
<223> OTHER INFORMATION: Xaa can be Gln or Gly
<220> FEATURE:
<221> NAME/KEY: misc_feature
<222> LOCATION: (13)..(13)
<223> OTHER INFORMATION: Xaa can be Tyr or Ala

<400> SEQUENCE: 9

Xaa Xaa Xaa Xaa Ser Pro Xaa Xaa Leu Xaa Xaa Xaa Xaa
1               5                   10


<210> SEQ ID NO 10
<211> LENGTH: 6
<212> TYPE: PRT
<213> ORGANISM: Artificial Sequence
<220> FEATURE:
<223> OTHER INFORMATION: Sythetic polypeptide
<220> FEATURE:
<221> NAME/KEY: misc_feature
<222> LOCATION: (3)..(3)
<223> OTHER INFORMATION: Xaa is a reactive electrophile
<220> FEATURE:
<221> NAME/KEY: misc_feature
<222> LOCATION: (4)..(4)
<223> OTHER INFORMATION: Xaa can be Gly or Pro
<220> FEATURE:
<221> NAME/KEY: misc_feature
<222> LOCATION: (6)..(6)
<223> OTHER INFORMATION: Xaa can be Tyr or His
```

<400> SEQUENCE: 10

Ser Pro Xaa Xaa Leu Xaa
1 5

<210> SEQ ID NO 11
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa is a reactive electrophile
<220> FEATURE:
<221> NAME/KEY: misc_feature
<222> LOCATION: (4)..(4)
<223> OTHER INFORMATION: Xaa can be Gly or Pro
<220> FEATURE:
<221> NAME/KEY: misc_feature
<222> LOCATION: (6)..(6)
<223> OTHER INFORMATION: Xaa can be Tyr or His
<220> FEATURE:
<221> NAME/KEY: misc_feature
<222> LOCATION: (7)..(7)
<223> OTHER INFORMATION: Xaa can be Arg or Leu

<400> SEQUENCE: 11

Ser Pro Xaa Xaa Leu Xaa Xaa
1 5

<210> SEQ ID NO 12
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa is a reactive electrophile
<220> FEATURE:
<221> NAME/KEY: misc_feature
<222> LOCATION: (4)..(4)
<223> OTHER INFORMATION: Xaa can be Gly or Pro
<220> FEATURE:
<221> NAME/KEY: misc_feature
<222> LOCATION: (6)..(6)
<223> OTHER INFORMATION: Xaa can be Tyr or His
<220> FEATURE:
<221> NAME/KEY: misc_feature
<222> LOCATION: (7)..(7)
<223> OTHER INFORMATION: Xaa can be Arg or Leu
<220> FEATURE:
<221> NAME/KEY: misc_feature
<222> LOCATION: (8)..(8)
<223> OTHER INFORMATION: Xaa can be Gln or Gly

<400> SEQUENCE: 12

Ser Pro Xaa Xaa Leu Xaa Xaa Xaa
1 5

<210> SEQ ID NO 13
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa is a reactive electrophile
<220> FEATURE:
<221> NAME/KEY: misc_feature
<222> LOCATION: (4)..(4)
<223> OTHER INFORMATION: Xaa can be Gly or Pro
<220> FEATURE:
<221> NAME/KEY: misc_feature
<222> LOCATION: (6)..(6)
<223> OTHER INFORMATION: Xaa can be Tyr or His
<220> FEATURE:
<221> NAME/KEY: misc_feature
<222> LOCATION: (7)..(7)
<223> OTHER INFORMATION: Xaa can be Arg or Leu
<220> FEATURE:
<221> NAME/KEY: misc_feature
<222> LOCATION: (8)..(8)
<223> OTHER INFORMATION: Xaa can be Gln or Gly
<220> FEATURE:
<221> NAME/KEY: misc_feature
<222> LOCATION: (9)..(9)
<223> OTHER INFORMATION: Xaa can be Tyr or Ala

<400> SEQUENCE: 13

Ser Pro Xaa Xaa Leu Xaa Xaa Xaa Xaa
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be Arg or Thr
<220> FEATURE:
<221> NAME/KEY: misc_feature
<222> LOCATION: (4)..(4)
<223> OTHER INFORMATION: Xaa is a reactive electrophile
<220> FEATURE:
<221> NAME/KEY: misc_feature
<222> LOCATION: (5)..(5)
<223> OTHER INFORMATION: Xaa can be Gly or Pro

<400> SEQUENCE: 14

Xaa Ser Pro Xaa Xaa Leu
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be Arg or Thr
<220> FEATURE:
<221> NAME/KEY: misc_feature
<222> LOCATION: (4)..(4)
<223> OTHER INFORMATION: Xaa is a reactive electrophile
<220> FEATURE:
<221> NAME/KEY: misc_feature
<222> LOCATION: (5)..(5)
<223> OTHER INFORMATION: Xaa can be Gly or Pro
<220> FEATURE:
<221> NAME/KEY: misc_feature
<222> LOCATION: (7)..(7)
<223> OTHER INFORMATION: Xaa can be Tyr or His

<400> SEQUENCE: 15

Xaa Ser Pro Xaa Xaa Leu Xaa
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be Arg or Thr
<220> FEATURE:
<221> NAME/KEY: misc_feature
<222> LOCATION: (4)..(4)
<223> OTHER INFORMATION: Xaa is a reactive electrophile
<220> FEATURE:
<221> NAME/KEY: misc_feature
<222> LOCATION: (5)..(5)
<223> OTHER INFORMATION: Xaa can be Gly or Pro
<220> FEATURE:
<221> NAME/KEY: misc_feature
<222> LOCATION: (7)..(7)
<223> OTHER INFORMATION: Xaa can be Tyr or His
<220> FEATURE:
<221> NAME/KEY: misc_feature
<222> LOCATION: (8)..(8)
<223> OTHER INFORMATION: Xaa can be Arg or Leu

<400> SEQUENCE: 16

Xaa Ser Pro Xaa Xaa Leu Xaa Xaa
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be Arg or Thr
<220> FEATURE:
<221> NAME/KEY: misc_feature
<222> LOCATION: (4)..(4)
<223> OTHER INFORMATION: Xaa is a reactive electrophile
<220> FEATURE:
<221> NAME/KEY: misc_feature
<222> LOCATION: (5)..(5)
<223> OTHER INFORMATION: Xaa can be Gly or Pro
<220> FEATURE:
<221> NAME/KEY: misc_feature
<222> LOCATION: (7)..(7)
<223> OTHER INFORMATION: Xaa can be Tyr or His
<220> FEATURE:
<221> NAME/KEY: misc_feature
<222> LOCATION: (8)..(8)
<223> OTHER INFORMATION: Xaa can be Arg or Leu
<220> FEATURE:
<221> NAME/KEY: misc_feature
<222> LOCATION: (9)..(9)
<223> OTHER INFORMATION: Xaa can be Gln or Gly

<400> SEQUENCE: 17

Xaa Ser Pro Xaa Xaa Leu Xaa Xaa Xaa
1               5

<210> SEQ ID NO 18
<211> LENGTH: 10
<212> TYPE: PRT
<213> ORGANISM: Artificial Sequence
<220> FEATURE:
<223> OTHER INFORMATION: Synthetic polypeptide
<220> FEATURE:

<221> NAME/KEY: misc_feature
<222> LOCATION: (1)..(1)
<223> OTHER INFORMATION: Xaa can be Arg or Thr
<220> FEATURE:
<221> NAME/KEY: misc_feature
<222> LOCATION: (4)..(4)
<223> OTHER INFORMATION: Xaa is a reactive electrophile
<220> FEATURE:
<221> NAME/KEY: misc_feature
<222> LOCATION: (5)..(5)
<223> OTHER INFORMATION: Xaa can be Gly or Pro
<220> FEATURE:
<221> NAME/KEY: misc_feature
<222> LOCATION: (7)..(7)
<223> OTHER INFORMATION: Xaa can be Tyr or His
<220> FEATURE:
<221> NAME/KEY: misc_feature
<222> LOCATION: (8)..(8)
<223> OTHER INFORMATION: Xaa can be Arg or Leu
<220> FEATURE:
<221> NAME/KEY: misc_feature
<222> LOCATION: (9)..(9)
<223> OTHER INFORMATION: Xaa can be Gln or Gly
<220> FEATURE:
<221> NAME/KEY: misc_feature
<222> LOCATION: (10)..(10)
<223> OTHER INFORMATION: Xaa can be Tyr or Ala

<400> SEQUENCE: 18

Xaa Ser Pro Xaa Xaa Leu Xaa Xaa Xaa Xaa
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be Pro or Leu
<220> FEATURE:
<221> NAME/KEY: misc_feature
<222> LOCATION: (2)..(2)
<223> OTHER INFORMATION: Xaa can be Arg or Thr
<220> FEATURE:
<221> NAME/KEY: misc_feature
<222> LOCATION: (5)..(5)
<223> OTHER INFORMATION: Xaa is a reactive electrophile
<220> FEATURE:
<221> NAME/KEY: misc_feature
<222> LOCATION: (6)..(6)
<223> OTHER INFORMATION: Xaa can be Gly or Pro

<400> SEQUENCE: 19

Xaa Xaa Ser Pro Xaa Xaa Leu
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be Pro or Leu
<220> FEATURE:
<221> NAME/KEY: misc_feature
<222> LOCATION: (2)..(2)
<223> OTHER INFORMATION: Xaa can be Arg or Thr
<220> FEATURE:
<221> NAME/KEY: misc_feature
<222> LOCATION: (5)..(5)
<223> OTHER INFORMATION: Xaa is a reactive electrophile
<220> FEATURE:
<221> NAME/KEY: misc_feature
<222> LOCATION: (6)..(6)
<223> OTHER INFORMATION: Xaa can be Gly or Pro
<220> FEATURE:
<221> NAME/KEY: misc_feature
<222> LOCATION: (8)..(8)
<223> OTHER INFORMATION: Xaa can be Tyr or His

<400> SEQUENCE: 20

Xaa Xaa Ser Pro Xaa Xaa Leu Xaa
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be Pro or Leu
<220> FEATURE:
<221> NAME/KEY: misc_feature
<222> LOCATION: (2)..(2)
<223> OTHER INFORMATION: Xaa can be Arg or Thr
<220> FEATURE:
<221> NAME/KEY: misc_feature
<222> LOCATION: (5)..(5)
<223> OTHER INFORMATION: Xaa is a reactive electrophile
<220> FEATURE:
<221> NAME/KEY: misc_feature
<222> LOCATION: (6)..(6)
<223> OTHER INFORMATION: Xaa can be Gly or Pro
<220> FEATURE:
<221> NAME/KEY: misc_feature
<222> LOCATION: (8)..(8)
<223> OTHER INFORMATION: Xaa can be Tyr or His
<220> FEATURE:
<221> NAME/KEY: misc_feature
<222> LOCATION: (9)..(9)
<223> OTHER INFORMATION: Xaa can be Arg or Leu

<400> SEQUENCE: 21

Xaa Xaa Ser Pro Xaa Xaa Leu Xaa Xaa
1               5

<210> SEQ ID NO 22
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be Pro or Leu
<220> FEATURE:
<221> NAME/KEY: misc_feature
<222> LOCATION: (2)..(2)
<223> OTHER INFORMATION: Xaa can be Arg or Thr
<220> FEATURE:
<221> NAME/KEY: misc_feature
<222> LOCATION: (5)..(5)
<223> OTHER INFORMATION: Xaa is a reactive electrophile
<220> FEATURE:
<221> NAME/KEY: misc_feature
<222> LOCATION: (6)..(6)
<223> OTHER INFORMATION: Xaa can be Gly or Pro
<220> FEATURE:
<221> NAME/KEY: misc_feature
<222> LOCATION: (8)..(8)

```
<223> OTHER INFORMATION: Xaa can be Tyr or His
<220> FEATURE:
<221> NAME/KEY: misc_feature
<222> LOCATION: (9)..(9)
<223> OTHER INFORMATION: Xaa can be Arg or Leu
<220> FEATURE:
<221> NAME/KEY: misc_feature
<222> LOCATION: (10)..(10)
<223> OTHER INFORMATION: Xaa can be Gln or Gly

<400> SEQUENCE: 22

Xaa Xaa Ser Pro Xaa Xaa Leu Xaa Xaa Xaa
1               5                   10


<210> SEQ ID NO 23
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be Pro or Leu
<220> FEATURE:
<221> NAME/KEY: misc_feature
<222> LOCATION: (2)..(2)
<223> OTHER INFORMATION: Xaa can be Arg or Thr
<220> FEATURE:
<221> NAME/KEY: misc_feature
<222> LOCATION: (5)..(5)
<223> OTHER INFORMATION: Xaa is a reactive electrophile
<220> FEATURE:
<221> NAME/KEY: misc_feature
<222> LOCATION: (6)..(6)
<223> OTHER INFORMATION: Xaa can be Gly or Pro
<220> FEATURE:
<221> NAME/KEY: misc_feature
<222> LOCATION: (8)..(8)
<223> OTHER INFORMATION: Xaa can be Tyr or His
<220> FEATURE:
<221> NAME/KEY: misc_feature
<222> LOCATION: (9)..(9)
<223> OTHER INFORMATION: Xaa can be Arg or Leu
<220> FEATURE:
<221> NAME/KEY: misc_feature
<222> LOCATION: (10)..(10)
<223> OTHER INFORMATION: Xaa can be Gln or Gly
<220> FEATURE:
<221> NAME/KEY: misc_feature
<222> LOCATION: (11)..(11)
<223> OTHER INFORMATION: Xaa can be Tyr or Ala

<400> SEQUENCE: 23

Xaa Xaa Ser Pro Xaa Xaa Leu Xaa Xaa Xaa Xaa
1               5                   10


<210> SEQ ID NO 24
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be Thr or Ser
<220> FEATURE:
<221> NAME/KEY: misc_feature
<222> LOCATION: (2)..(2)
<223> OTHER INFORMATION: Xaa can be Pro or Leu
<220> FEATURE:
<221> NAME/KEY: misc_feature
<222> LOCATION: (3)..(3)
<223> OTHER INFORMATION: Xaa can be Arg or Thr
```

<220> FEATURE:
<221> NAME/KEY: misc_feature
<222> LOCATION: (6)..(6)
<223> OTHER INFORMATION: Xaa is a reactive electrophile
<220> FEATURE:
<221> NAME/KEY: misc_feature
<222> LOCATION: (7)..(7)
<223> OTHER INFORMATION: Xaa can be Gly or Pro

<400> SEQUENCE: 24

Xaa Xaa Xaa Ser Pro Xaa Xaa Leu
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be Thr or Ser
<220> FEATURE:
<221> NAME/KEY: misc_feature
<222> LOCATION: (2)..(2)
<223> OTHER INFORMATION: Xaa can be Pro or Leu
<220> FEATURE:
<221> NAME/KEY: misc_feature
<222> LOCATION: (3)..(3)
<223> OTHER INFORMATION: Xaa can be Arg or Thr
<220> FEATURE:
<221> NAME/KEY: misc_feature
<222> LOCATION: (6)..(6)
<223> OTHER INFORMATION: Xaa is a reactive electrophile
<220> FEATURE:
<221> NAME/KEY: misc_feature
<222> LOCATION: (7)..(7)
<223> OTHER INFORMATION: Xaa can be Gly or Pro
<220> FEATURE:
<221> NAME/KEY: misc_feature
<222> LOCATION: (9)..(9)
<223> OTHER INFORMATION: Xaa can be Tyr or His

<400> SEQUENCE: 25

Xaa Xaa Xaa Ser Pro Xaa Xaa Leu Xaa
1               5

<210> SEQ ID NO 26
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be Thr or Ser
<220> FEATURE:
<221> NAME/KEY: misc_feature
<222> LOCATION: (2)..(2)
<223> OTHER INFORMATION: Xaa can be Pro or Leu
<220> FEATURE:
<221> NAME/KEY: misc_feature
<222> LOCATION: (3)..(3)
<223> OTHER INFORMATION: Xaa can be Arg or Thr
<220> FEATURE:
<221> NAME/KEY: misc_feature
<222> LOCATION: (6)..(6)
<223> OTHER INFORMATION: Xaa is a reactive electrophile
<220> FEATURE:
<221> NAME/KEY: misc_feature
<222> LOCATION: (7)..(7)
<223> OTHER INFORMATION: Xaa can be Gly or Pro
<220> FEATURE:

<221> NAME/KEY: misc_feature
<222> LOCATION: (9)..(9)
<223> OTHER INFORMATION: Xaa can be Tyr or His
<220> FEATURE:
<221> NAME/KEY: misc_feature
<222> LOCATION: (10)..(10)
<223> OTHER INFORMATION: Xaa can be Arg or Leu

<400> SEQUENCE: 26

Xaa Xaa Xaa Ser Pro Xaa Xaa Leu Xaa Xaa
1 5 10

<210> SEQ ID NO 27
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be Thr or Ser
<220> FEATURE:
<221> NAME/KEY: misc_feature
<222> LOCATION: (2)..(2)
<223> OTHER INFORMATION: Xaa can be Pro or Leu
<220> FEATURE:
<221> NAME/KEY: misc_feature
<222> LOCATION: (3)..(3)
<223> OTHER INFORMATION: Xaa can be Arg or Thr
<220> FEATURE:
<221> NAME/KEY: misc_feature
<222> LOCATION: (6)..(6)
<223> OTHER INFORMATION: Xaa is a reactive electrophile
<220> FEATURE:
<221> NAME/KEY: misc_feature
<222> LOCATION: (7)..(7)
<223> OTHER INFORMATION: Xaa can be Gly or Pro
<220> FEATURE:
<221> NAME/KEY: misc_feature
<222> LOCATION: (9)..(9)
<223> OTHER INFORMATION: Xaa can be Tyr or His
<220> FEATURE:
<221> NAME/KEY: misc_feature
<222> LOCATION: (10)..(10)
<223> OTHER INFORMATION: Xaa can be Arg or Leu
<220> FEATURE:
<221> NAME/KEY: misc_feature
<222> LOCATION: (11)..(11)
<223> OTHER INFORMATION: Xaa can be Gln or Gly

<400> SEQUENCE: 27

Xaa Xaa Xaa Ser Pro Xaa Xaa Leu Xaa Xaa Xaa
1 5 10

<210> SEQ ID NO 28
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be Thr or Ser
<220> FEATURE:
<221> NAME/KEY: misc_feature
<222> LOCATION: (2)..(2)
<223> OTHER INFORMATION: Xaa can be Pro or Leu
<220> FEATURE:
<221> NAME/KEY: misc_feature
<222> LOCATION: (3)..(3)
<223> OTHER INFORMATION: Xaa can be Arg or Thr
<220> FEATURE:
<221> NAME/KEY: misc_feature
<222> LOCATION: (6)..(6)
<223> OTHER INFORMATION: Xaa is a reactive electrophile
<220> FEATURE:
<221> NAME/KEY: misc_feature
<222> LOCATION: (7)..(7)
<223> OTHER INFORMATION: Xaa can be Gly or Pro
<220> FEATURE:
<221> NAME/KEY: misc_feature
<222> LOCATION: (9)..(9)
<223> OTHER INFORMATION: Xaa can be Tyr or His
<220> FEATURE:
<221> NAME/KEY: misc_feature
<222> LOCATION: (10)..(10)
<223> OTHER INFORMATION: Xaa can be Arg or Leu
<220> FEATURE:
<221> NAME/KEY: misc_feature
<222> LOCATION: (11)..(11)
<223> OTHER INFORMATION: Xaa can be Gln or Gly
<220> FEATURE:
<221> NAME/KEY: misc_feature
<222> LOCATION: (12)..(12)
<223> OTHER INFORMATION: Xaa can be Tyr or Ala

<400> SEQUENCE: 28

```
Xaa Xaa Xaa Ser Pro Xaa Xaa Leu Xaa Xaa Xaa Xaa
1               5                   10
```

<210> SEQ ID NO 29
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be Phe or Thr
<220> FEATURE:
<221> NAME/KEY: misc_feature
<222> LOCATION: (2)..(2)
<223> OTHER INFORMATION: Xaa can be Thr or Ser
<220> FEATURE:
<221> NAME/KEY: misc_feature
<222> LOCATION: (3)..(3)
<223> OTHER INFORMATION: Xaa can be Pro or Leu
<220> FEATURE:
<221> NAME/KEY: misc_feature
<222> LOCATION: (4)..(4)
<223> OTHER INFORMATION: Xaa can be Arg or Thr
<220> FEATURE:
<221> NAME/KEY: misc_feature
<222> LOCATION: (7)..(7)
<223> OTHER INFORMATION: Xaa is a reactive electrophile
<220> FEATURE:
<221> NAME/KEY: misc_feature
<222> LOCATION: (8)..(8)
<223> OTHER INFORMATION: Xaa can be Gly or Pro

<400> SEQUENCE: 29

```
Xaa Xaa Xaa Xaa Ser Pro Xaa Xaa Leu
1               5
```

<210> SEQ ID NO 30
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be Phe or Thr
<220> FEATURE:
<221> NAME/KEY: misc_feature
<222> LOCATION: (2)..(2)

<223> OTHER INFORMATION: Xaa can be Thr or Ser
<220> FEATURE:
<221> NAME/KEY: misc_feature
<222> LOCATION: (3)..(3)
<223> OTHER INFORMATION: Xaa can be Pro or Leu
<220> FEATURE:
<221> NAME/KEY: misc_feature
<222> LOCATION: (4)..(4)
<223> OTHER INFORMATION: Xaa can be Arg or Thr
<220> FEATURE:
<221> NAME/KEY: misc_feature
<222> LOCATION: (7)..(7)
<223> OTHER INFORMATION: Xaa is a reactive electrophile
<220> FEATURE:
<221> NAME/KEY: misc_feature
<222> LOCATION: (8)..(8)
<223> OTHER INFORMATION: Xaa can be Gly or Pro
<220> FEATURE:
<221> NAME/KEY: misc_feature
<222> LOCATION: (10)..(10)
<223> OTHER INFORMATION: Xaa can be Tyr or His

<400> SEQUENCE: 30

Xaa Xaa Xaa Xaa Ser Pro Xaa Xaa Leu Xaa
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be Phe or Thr
<220> FEATURE:
<221> NAME/KEY: misc_feature
<222> LOCATION: (2)..(2)
<223> OTHER INFORMATION: Xaa can be Thr or Ser
<220> FEATURE:
<221> NAME/KEY: misc_feature
<222> LOCATION: (3)..(3)
<223> OTHER INFORMATION: Xaa can be Pro or Leu
<220> FEATURE:
<221> NAME/KEY: misc_feature
<222> LOCATION: (4)..(4)
<223> OTHER INFORMATION: Xaa can be Arg or Thr
<220> FEATURE:
<221> NAME/KEY: misc_feature
<222> LOCATION: (7)..(7)
<223> OTHER INFORMATION: Xaa is a reactive electrophile
<220> FEATURE:
<221> NAME/KEY: misc_feature
<222> LOCATION: (8)..(8)
<223> OTHER INFORMATION: Xaa can be Gly or Pro
<220> FEATURE:
<221> NAME/KEY: misc_feature
<222> LOCATION: (10)..(10)
<223> OTHER INFORMATION: Xaa can be Tyr or His
<220> FEATURE:
<221> NAME/KEY: misc_feature
<222> LOCATION: (11)..(11)
<223> OTHER INFORMATION: Xaa can be Arg or Leu

<400> SEQUENCE: 31

Xaa Xaa Xaa Xaa Ser Pro Xaa Xaa Leu Xaa Xaa
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be Phe or Thr
<220> FEATURE:
<221> NAME/KEY: misc_feature
<222> LOCATION: (2)..(2)
<223> OTHER INFORMATION: Xaa can be Thr or Ser
<220> FEATURE:
<221> NAME/KEY: misc_feature
<222> LOCATION: (3)..(3)
<223> OTHER INFORMATION: Xaa can be Pro or Leu
<220> FEATURE:
<221> NAME/KEY: misc_feature
<222> LOCATION: (4)..(4)
<223> OTHER INFORMATION: Xaa can be Arg or Thr
<220> FEATURE:
<221> NAME/KEY: misc_feature
<222> LOCATION: (7)..(7)
<223> OTHER INFORMATION: Xaa is a reactive electrophile
<220> FEATURE:
<221> NAME/KEY: misc_feature
<222> LOCATION: (8)..(8)
<223> OTHER INFORMATION: Xaa can be Gly or Pro
<220> FEATURE:
<221> NAME/KEY: misc_feature
<222> LOCATION: (10)..(10)
<223> OTHER INFORMATION: Xaa can be Tyr or His
<220> FEATURE:
<221> NAME/KEY: misc_feature
<222> LOCATION: (11)..(11)
<223> OTHER INFORMATION: Xaa can be Arg or Leu
<220> FEATURE:
<221> NAME/KEY: misc_feature
<222> LOCATION: (12)..(12)
<223> OTHER INFORMATION: Xaa can be Gln or Gly

<400> SEQUENCE: 32

```
Xaa Xaa Xaa Xaa Ser Pro Xaa Xaa Leu Xaa Xaa Xaa
1               5                   10
```

<210> SEQ ID NO 33
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa is a reactive electrophile

<400> SEQUENCE: 33

```
Ser Pro Xaa Gly Leu
1               5
```

<210> SEQ ID NO 34
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa is a reactive electrophile

<400> SEQUENCE: 34

```
Ser Pro Xaa Pro Leu
1               5
```

<210> SEQ ID NO 35
<211> LENGTH: 5

-continued

```
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 35

Ser Pro Cys Xaa Leu
1               5
```

COVALENT INHIBITORS OF DUAL OXIDASE 1 (DUOX 1)

RELATED APPLICATIONS

This application claims the benefit of U.S. Provisional Patent Application Ser. No. 62/245,114, filed Oct. 22, 2015, entitled "Covalent Inhibitors of Dual Oxidase 1 (DUOX1)," incorporated herein by reference in its entirety.

GOVERNMENT FUNDING

This invention was made with government support under Grant Nos. HL085646 and ES021476 awarded by National Institutes of Health. The government has certain rights in the invention.

FIELD

The present invention generally relates to inhibitors of DUOX1.

BACKGROUND

The NOX (NADPH oxidase) homolog, dual oxidase 1 (DUOX1), is expressed in the airway epithelium, and contributes to epithelial responses for various environmental triggers, such as allergens, by an oxidant-dependent cell signaling mechanism. DUOX1 is important in the allergen-induced epithelial production of the cytokine IL-33, which is a strong determinant of allergic asthma. DUOX1 may be enhanced in subjects with allergic asthma. DUOX1 may also contribute to several features of allergic asthma, such as TH2 cytokine production, mucus metaplasia, airway remodeling with subepithelial collagen deposition, and airway hyperresponsiveness, based on mice models. However, although antioxidant-based approaches have been successful in inhibiting allergic asthma in animal models, such approaches have not translated well to human asthma. Pharmacological approaches to target NOX enzymes have primarily targeted NADPH oxidase activation mechanisms that are not applicable to DUOX1, and so far none have been tested towards DUOX1. Accordingly, the inhibition of DUOX1 has not been well studied.

SUMMARY

The present invention generally relates to inhibitors of DUOX1. The subject matter of the present invention involves, in some cases, interrelated products, alternative solutions to a particular problem, and/or a plurality of different uses of one or more systems and/or articles.

In one aspect, the present invention is generally directed to a composition. In accordance with a first set of embodiments, the composition comprises a peptide comprising a sequence S-P-Re-J-L (SEQ ID NO: 8), where Re is a reactive electrophile and J is G or P.

The present invention, in another aspect, is generally directed to a method. In one set of embodiments, the method comprises administering, to a subject, a composition comprising a peptide comprising a sequence S-P-Re-J-L (SEQ ID NO: 8), where Re is a reactive electrophile and J is G or P.

The method, in another set of embodiments, includes reacting a peptide with DUOX1, wherein the peptide comprises a sequence S-P-Re-J-L (SEQ ID NO: 8), Re being a reactive electrophile and J being G or P. In some cases, the Re of the peptide covalently binds to a cysteine within the DUOX1.

In one set of embodiments, the present invention is generally directed to a method comprising administering, to a subject, an aerosol comprising dimethylfumarate, curcumin, and/or sulforaphane. In another set of embodiments, the present invention is generally directed to a composition comprising aerosolized particles comprising dimethyl fumarate, curcumin, and/or sulforaphane. In still another set of embodiments, the present invention is generally directed to an inhaler comprising a comprising dimethyl fumarate, curcumin, and/or sulforaphane. In yet another set of embodiments, the present invention is generally directed to a method comprising reacting dimethyl fumarate, curcumin, and/or sulforaphane with DUOX1 within the lungs of a subject.

In another aspect, the present invention is generally directed to a method comprising administering, to a subject, an aerosol comprising a DUOX1 inhibitor, e.g., at a concentration of at least 90 ppm. In one set of embodiments, the present invention is generally directed to a composition, comprising aerosolized particles comprising a DUOX1 inhibitor. The present invention, in accordance with another set of embodiments, includes an inhaler comprising a comprising a DUOX1 inhibitor. The present invention, in still another set of embodiments is generally directed to reacting a DUOX1 inhibitor with DUOX1 in a subject, for example, within the lungs, the skin, the eyes, etc., of a subject. Examples of DUOX1 inhibitors include, but are not limited to, hydroxynonenal, curcumin, sulforaphane, cinnamaldehyde, dimethyl fumarate, and phenyl vinyl sulfonate.

Several methods are disclosed herein of administering a subject with a compound for prevention or treatment of a particular condition. It is to be understood that in each such aspect of the invention, the invention specifically includes, also, the compound for use in the treatment or prevention of that particular condition, as well as use of the compound for the manufacture of a medicament for the treatment or prevention of that particular condition.

In another aspect, the present invention encompasses methods of making one or more of the embodiments described herein, for example, an inhibitor of DUOX1. In still another aspect, the present invention encompasses methods of using one or more of the embodiments described herein, for example, an inhibitor of DUOX1.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 1A-1C generally illustrate delivery of acrolein in accordance with one embodiment;

FIG. 2 illustrates electrophilic inhibition data, in another embodiment;

FIG. 3 illustrates acrolein pretreatment effects, according to yet another embodiment;

FIGS. 4A-4C illustrate dose-dependent inhibition with various electrophiles, in certain embodiments of the invention;

FIGS. 7A-7C schematically illustrate drug binding, according to certain embodiments of the invention;

FIGS. 8A-8C illustrate sequence similarity of DUOX1 and DUOXA1 proteins;

FIG. 11 illustrates the sequence of DUOX1.

DETAILED DESCRIPTION

Figure 5:
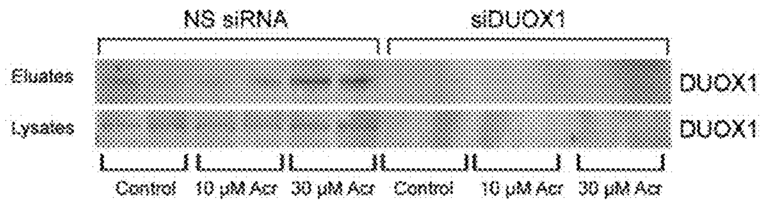
FIG. 5 illustrates data illustrative DUOX1 targeting by acrolein, in still another embodiment.

The present invention generally relates to inhibitors of DUOX1. In some aspects, an inhibitor may be applied to a subject having or being at risk for asthma or other conditions. The inhibitor may be applied by various techniques, such as pulmonary or topical delivery. In some embodiments, the inhibitor may include a peptide or other moiety having a reactive electrophile. The reactive electrophile can target cysteine or other residues within DUOX1 to inhibit its activity, e.g., by covalently binding to the residue. Other non-limiting examples of suitable inhibitors include hydroxynonenal, curcumin, sulforaphane, cinnamaldehyde, dimethyl fumarate, or phenyl vinyl sulfonate. Other aspects of the invention are generally directed to methods of making or using such inhibitors, kits involving such inhibitors, devices or formulations containing such inhibitors, or the like.

Thus, one aspect of the present invention is generally directed to compositions comprising reactive electrophiles. Without wishing to be bound by any theory, it is believed that certain reactive electrophiles may inhibit DUOX1. Compositions containing such reactive electrophiles may be used to treat various allergic diseases, such as asthma or allergic rhinitis (e.g., in inhalers or using pulmonary delivery), allergic skin disorders such as atopic dermatitis or psoriasis (e.g., using topical administration), or other allergic conditions such as allergic conjunctivitis. The reactive electrophiles may inhibit DUOX1, which is expressed in the airway epithelium, and may contribute to epithelial responses to various environmental triggers, such as allergens, by an oxidant-dependent cell signaling mechanism, which may thus trigger asthmatic or other allergic attacks. The structure of human DUOX1 is shown in FIG. 7A, and the amino acid sequence is listed in FIG. 11. Accordingly, according to certain embodiments of the invention, it is believed that inhibition of DUOX1 may be useful in treating various allergic diseases such as these.

Asthma generally refers to a disorder of the respiratory system characterized by inflammation, narrowing of the airways, and/or increased reactivity of the airways to inhaled agents. However, asthma is not a well-understood disease. Asthma is frequently, although not exclusively, associated with atopic or allergic symptoms. As used herein, a subject having asthma includes those subjects that have been identified as having asthma but that do not have the active disease during treatment, as well as subjects that have the active disease of asthma.

Certain reactive electrophiles are able to bind to cysteines on the DUOX1, and these may cause inhibition of DUOX1, which may lessen or prevent activity of DUOX1, which may thus lessen responses to various environmental triggers, e.g., during an asthmatic attack or other allergic reaction. In some cases, the reactive electrophiles can bind to certain cysteine residues (e.g., residues 4, 118, 345, 364, 423, 564, and 579) within the peroxidase homology domain of DUOX1. The binding to cysteine by the reactive electrophile is typically covalent, and may be reversible.

Examples of reactive electrophile functional groups that are able to react with cysteine include alkylenes such as terminal alkylenes, vinyl sulfones, or maleimide functional moieties. Thus, in some embodiments, the reactive electrophile comprises one or more of these moieties. Specific non-limiting examples of such reactive electrophile moieties (e.g., as side chains in a peptide, or having a configuration $NH_2$—CH(Re)—COOH) include:

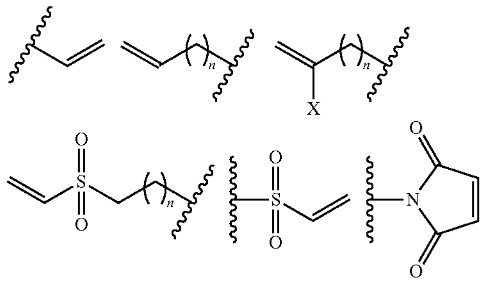
, where n is any suitable integer (e.g., 0, 1, 2, 3, 4, etc.), and X (where present) is H or a halogen, e.g., F, Cl, Br, etc. In some embodiments, n is 0, 1, or 2. In some embodiments, X is H, F, or Cl. See, e.g., FIG. 10, showing reactive electrophile functional groups as side chains within a peptide.

As an example, the reactive electrophile may be present within a peptide. The peptide may be prepared using any suitable technique known to those of ordinary skill in the art, e.g., solid-state polypeptide synthesis. The peptide may include any number of residues and include a reactive electrophile, e.g., as a side chain within the peptide. Non-limiting examples of incorporating a reactive electrophile within a peptide includes those described herein. In some cases, the peptide may have 5, 6, 7, 8, or 9 residues, or other numbers of residues in some embodiments. The reactive electrophile within the peptide may be, for example, an alkylene, a vinyl sulfone, a maleimide, etc., including any of the ones described herein. It should be noted that the reactive electrophile within the protein may be one that is not a naturally-occurring amino acid residue.

As specific non-limiting examples, in one set of embodiments, the peptide may comprise or consist essentially of a sequence:

S-P-Re-J-L (SEQ ID NO: 8), where Re is a reactive electrophile and J is G or P (using the commonly-accepted one-letter abbreviations for amino acids, i.e., glycine or proline). The reactive electrophile may include any of the ones discussed herein. In some cases, the peptide is 5 residues long, although in some cases, the above sequence may be part of a longer oligopeptide chain. As non-limiting examples, the peptide may be part of a sequence such as:

$Z^4$-$Z^3$-$Z^2$-$Z^1$-S-P-Re-J-L-$Z^5$-$Z^6$-$Z^7$-$Z^8$ (SEQ ID NO: 9), where each numbered Z is independently an amino acid. In addition, in some embodiments, one or more of the ending Z's may be absent, e.g., thereby forming a shorter peptide. Thus, examples of suitable peptide sequences include the following:

S-P-Re-J-L-$Z^5$ (SEQ ID NO: 10)

S-P-Re-J-L-$Z^5$-$Z^6$ (SEQ ID NO: 11)

S-P-Re-J-L-$Z^5$-$Z^6$-$Z^7$ (SEQ ID NO: 12)

S-P-Re-J-L-$Z^5$-$Z^6$-$Z^7$-$Z^8$ (SEQ ID NO: 13)

$Z^1$-S-P-Re-J-L (SEQ ID NO: 14)

$Z^1$-S-P-Re-J-L-$Z^5$ (SEQ ID NO: 15)

$Z^1$-S-P-Re-J-L-$Z^5$-$Z^6$ (SEQ ID NO: 16)

$Z^1$-S-P-Re-J-L-$Z^5$-$Z^6$-$Z^7$ (SEQ ID NO: 17)

$Z^1$-S-P-Re-J-L-$Z^5$-$Z^6$-$Z^7$-$Z^8$ (SEQ ID NO: 18)

$Z^2$-$Z^1$-S-P-Re-J-L (SEQ ID NO: 19)

$Z^2$-$Z^1$-S-P-Re-J-L-$Z^5$ (SEQ ID NO: 20)

$Z^2$-$Z^1$-S-P-Re-J-L-$Z^5$-$Z^6$ (SEQ ID NO: 21)

$Z^2$-$Z^1$-S-P-Re-J-L-$Z^5$-$Z^6$-$Z^7$ (SEQ ID NO: 22)

$Z^2$-$Z^1$-S-P-Re-J-L-$Z^5$-$Z^6$-$Z^7$-$Z^8$ (SEQ ID NO: 23)

$Z^3$-$Z^2$-$Z^1$-S-P-Re-J-L (SEQ ID NO: 24)

$Z^3$-$Z^2$-$Z^1$-S-P-Re-J-L-$Z^5$ (SEQ ID NO: 25)

$Z^3$-$Z^2$-$Z^1$-S-P-Re-J-L-$Z^5$-$Z^6$ (SEQ ID NO: 26)

$Z^3$-$Z^2$-$Z^1$-S-P-Re-J-L-$Z^5$-$Z^6$-$Z^7$ (SEQ ID NO: 27)

$Z^3$-$Z^2$-$Z^1$-S-P-Re-J-L-$Z^5$-$Z^6$-$Z^7$-$Z^8$ (SEQ ID NO: 28)

$Z^4$-$Z^3$-$Z^2$-$Z^1$-S-P-Re-J-L (SEQ ID NO: 29)

$Z^4$-$Z^3$-$Z^2$-$Z^1$-S-P-Re-J-L-$Z^5$ (SEQ ID NO: 30)

$Z^4$-$Z^3$-$Z^2$-$Z^1$-S-P-Re-J-L-$Z^5$-$Z^6$ (SEQ ID NO: 31)

$Z^4$-$Z^3$-$Z^2$-$Z^1$-S-P-Re-J-L-$Z^5$-$Z^6$-$Z^7$ (SEQ ID NO: 32).

As before, the above sequences may represent the whole peptide, or a portion of a longer oligopeptide chain. Each Z may independently be an amino acid. The amino acid may be a naturally-occurring amino acid, e.g., one of the 20 amino acids commonly found in nature, typically in the L-isomer, i.e., alanine ("Ala" or "A"), arginine ("Arg" or "R"), asparagine ("Asn" or "N"), aspartic acid ("Asp" or "D"), cysteine ("Cys" or "C"), glutamine ("Gln" or "Q"), glutamic acid ("Glu" or "E"), glycine ("Gly" or "G"), histidine ("His" or "H"), isoleucine ("Ile" or "I"), leucine ("Leu" or "L"), lysine ("Lys" or "K"), methionine ("Met" or "M"), phenylalaine ("Phe" or "F"), proline ("Pro" or "P"), serine ("Ser" or "S"), threonine ("Thr" or "T"), tryptophan ("Trp" or "W"), tyrosine ("Tyr" or "Y"), and valine ("Val" or "V"). In some embodiments, independently, one, two, three, or more of the following may be present: $Z^1$ is R or T, $Z^2$ is P or L, $Z^3$ is T or S, $Z^4$ is F or T, $Z^5$ is Y or H, $Z^6$ is R or L, $Z^7$ is Q or G, and $Z^8$ is Y or A. In addition, a Z may also independently be, in some cases, an amino acid that is not one of the naturally-occurring amino acids.

The reactive electrophile may also be present within other molecules. For example, the reactive entity may be attached to an organic moiety, such as a phenyl group (e.g., phenyl vinyl sulfonate). In some cases, the small molecule may have a molecular weight of less than about 2000 Da or less than about 1000 Da. Other examples of reactive electrophiles, but are not limited to, hydroxynonenal, curcumin, sulforaphane, cinnamaldehyde, or dimethylfumarate.

In some embodiments, the composition may be administered to a subject, e.g., to the lungs of a subject, or to another area where allergic reaction may occur, e.g., the skin. In some cases, the composition may be systemically delivered. The composition may also be contained within a suitable pharmaceutically acceptable carrier. As discussed herein, in certain aspects, a composition may be administered to a subject having or at risk of a disease or condition characterized by elevated DUOX1, such as asthma or other allergic diseases. As previously discussed, it is believed that reactive electrophiles may inhibit DUOX1. The subject may have or be at risk of various allergic disease such as asthma, allergic rhinitis, allergic skin disorders such as atopic dermatitis or psoriasis, or other allergic conditions such as allergic conjunctivitis. For instance, the asthma may be triggered by house dust mites, *alternaria alternata*, or other allergens that may be found in the environment. In some cases the allergens are not well-characterized. The composition may be given, for instance, via pulmonary delivery or by topical application, e.g., to the skin or eyes.

If the composition is delivered to the lungs of a subject, the composition may, in some cases, be contained within an aerosol that can be delivered to the lungs. For instance, the composition may be contained within suitable particles or liquid that can be readily aerosolized, e.g., into particles or droplets, that can be delivered to the lungs. For example, the composition may be aerosolized using a suitable inhaler, e.g., a particle or liquid inhaler. Many such inhalers can be readily obtained commercially. In some embodiments, the particles or droplets may have a mass median aerodynamic diameter of no more than about 10 micrometers, no more than about 5 micrometers, or no more than about 1 micrometer, for delivery to the lungs. The mass median aerodynamic diameter is the diameter at which 50% of the particles by mass are larger and 50% are smaller. Pulmonary delivery may be useful, for instance, in the treatment of certain allergic conditions such as asthma or allergic rhinitis.

In another set of embodiments, the composition may be applied topically to the skin of a subject, e.g., to treat certain allergic skin disorders such as atopic dermatitis or psoriasis. For instance, the composition may be formed as a cream, foam, gel, lotion, or ointment that can be applied to a portion of the skin, e.g., which exhibits syndromes of atopic dermatitis or psoriasis.

In certain embodiments, any composition of the present invention may be administered to a subject, either by itself and/or in conjunction with co-factors, other therapeutics, or the like. For example, the composition may include a DUOX1 inhibitor, for example, a peptide or small molecule as discussed herein, e.g., containing a reactive electrophile. When administered, the compositions of the invention can be applied in a therapeutically effective, pharmaceutically acceptable amount as a pharmaceutically acceptable formulation, for example, a pharmaceutically acceptable carrier such as those described below. The term "effective amount" of a composition refers to the amount necessary or sufficient to realize a desired biologic effect, e.g., treatment or prevention of asthma or other allergic reaction as discussed herein (e.g., an allergic skin disorder). Combined with the teachings provided herein, by choosing among the various active compositions and weighing factors such as potency, relative bioavailability, patient body weight, severity of adverse side effects and preferred mode of administration, an effective prophylactic or therapeutic treatment regimen can be planned which does not cause substantial toxicity and yet is effective to treat the particular subject. The effective amount for any particular application can vary depending on such factors as the disease or condition being treated, the particular composition being administered the size of the subject, or the severity of the disease or condition. One of ordinary skill in the art can empirically determine the effective amount of a particular composition and/or other therapeutic agent without necessitating undue experimentation.

The terms "treat," "treated," "treating," and the like, generally refer to administration of the compositions to a subject which may increase the resistance of the subject to development or further development of the condition, to administration of the composition after the subject has developed the condition in order to eliminate or at least control development of the condition, and/or slow the progression of or to reduce the severity of symptoms caused by the condition. When administered to a subject, effective amounts will depend on the particular condition being treated and the desired outcome. A therapeutically effective dose may be determined by those of ordinary skill in the art, for instance, employing factors such as those further described below and using no more than routine experimentation.

For use in therapy, an effective amount of the compositions of the present invention can be administered to a subject by any mode that delivers the composition to the desired surface, e.g., through pulmonary or topical delivery. Administering the pharmaceutical composition of the present invention may be accomplished by any technique known to the skilled artisan. Other examples of routes of administration include but are not limited to oral, parenteral, intramuscular, intranasal, sublingual, intratracheal, inhalation, topical, ocular, vaginal, intravenously, percutaneously, and rectal.

In administering the compositions of the invention to a subject, dosing amounts, dosing schedules, routes of administration, and the like may be selected so as to affect known activities of these compositions. Dosages may be estimated based on the results of experimental models, optionally in combination with the results of assays of compositions of the present invention. Dosage may be adjusted appropriately to achieve desired drug levels, local or systemic, depending upon the mode of administration. The doses may be given in one or several administrations per day. Multiple doses per day are also contemplated in some cases to achieve appropriate systemic levels of the composition within the subject or within the active site of the subject.

The dose of the composition to the subject may be such that a therapeutically effective amount of the composition reaches an active site of the composition within the subject. The dosage may be given in some cases at the maximum amount while avoiding or minimizing any potentially detrimental side effects within the subject. The dosage of the composition that is actually administered is dependent upon factors such as the final concentration desired at the active site, the method of administration to the subject, the efficacy of the composition, the longevity of the composition within the subject, the timing of administration, the effect of concurrent treatments (e.g., as in a cocktail), etc. The dose delivered may also depend on conditions associated with the subject, and can vary from subject to subject in some cases. For example, the age, sex, weight, size, environment, physical conditions, or current state of health of the subject may also influence the dose required and/or the concentration of the composition at the active site. Variations in dosing may occur between different individuals or even within the same individual on different days. It may be preferred that a maximum dose be used, that is, the highest safe dose according to sound medical judgment. Preferably, the dosage form is such that it does not substantially deleteriously affect the subject.

Subject doses of the compositions described herein for pulmonary or topical delivery may range from about 0.1 microgram to 10 mg per administration, which depending on the application could be given daily, weekly, or monthly and any other amount of time therebetween. Other examples of pulmonary or topical doses range from about 0.01 mg to about 1 mg per administration, about 10 microgram to 5 mg per administration, or about 100 microgram to 1 mg, with 2 to 4 administrations being spaced days or weeks apart. Doses may also range from 1 microgram to 10 mg per administration, and most typically 10 microgram to 1 mg, with daily or weekly administrations. The compositions of the present invention may be administered in single or multiple doses over extended period of time. For any composition described herein the therapeutically effective amount can be initially determined from animal models. The applied dose can be adjusted based on the relative bioavailability and potency of the administered composition. Adjusting the dose to achieve maximal efficacy based on the methods described above and other methods as are well-known in the art is well within the capabilities of the ordinarily skilled artisan.

The treatments disclosed herein may be given to any subject, for example, a human, or a non-human animal, such as a dog, a cat, a horse, a rabbit, a cow, a pig, a sheep, a goat, a rat (e.g., *Rattus Norvegicus*), a mouse (e.g., *Mus musculus*), a guinea pig, a non-human primate (e.g., a monkey, a chimpanzee, a baboon, an ape, a gorilla, etc.), or the like.

In certain embodiments, a composition of the invention is administered to a subject who has a family history of a condition such as asthma or other allergic condition, or to a subject who has a genetic predisposition for such conditions. In yet other embodiments, the compositions is administered to subjects who exhibit symptoms of the condition (e.g., early or advanced). In still other embodiments, the composition may be administered to a subject as a preventive measure. In some embodiments, the composition may be administered to a subject based on demographics or epidemiological studies, or to a subject in a particular field or career.

Administration of a composition of the invention may be accomplished by any medically acceptable method which allows the composition to reach its target. The particular mode selected will depend of course, upon factors such as those previously described, for example, the particular composition, the severity of the state of the subject being treated, the dosage required for therapeutic efficacy, etc. As used herein, a "medically acceptable" mode of treatment is a mode able to produce effective levels of the composition within the subject without causing clinically unacceptable adverse effects.

Any medically acceptable method may be used to administer the composition to the subject. The administration may be localized (i.e., to a particular region, such as the lungs or a specific region of the skin) or systemic, depending on the condition to be treated. For example, the composition may be administered orally, vaginally, rectally, buccally, pulmonary, topically, nasally, transdermally, through parenteral injection or implantation, via surgical administration, or any other method of administration where access to the target by the composition of the invention is achieved.

In one set of embodiments, the compositions of the invention are administered by inhalation. For administration by inhalation, the compositions for use according to various embodiments may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the composition and a suitable powder base such as lactose or starch.

Contemplated herein is pulmonary delivery of certain compositions of the present invention. The compositions may be delivered to the lungs of a mammal while inhaling. Also contemplated for use in some embodiments of the invention are a wide range of mechanical devices designed for pulmonary delivery of therapeutic products, including but not limited to nebulizers, metered dose inhalers, and powder inhalers, all of which are familiar to those skilled in the art. Some non-limiting specific examples of commercially available devices are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

Certain devices require the use of various formulations suitable for the dispensing of some compositions of the present invention. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated for certain embodiments. Chemically modified systems may also be prepared in different formulations depending on the type of chemical modification or the type of device employed.

Some formulations suitable for use with a nebulizer, either jet or ultrasonic, will typically comprise a composition as described herein, dissolved in water at a concentration of about 0.1 to 25 mg of biologically active composition per mL of solution. The formulation may also include a buffer and a simple sugar (e.g., for stabilization of the composition and regulation of osmotic pressure). The nebulizer formulation may also contain a surfactant to reduce or prevent surface induced aggregation caused by atomization of the solution in forming the aerosol.

Certain formulations for use with a metered-dose inhaler device may generally comprise a finely divided powder containing a composition as described herein, suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device may comprise a finely divided dry powder containing a composition as described herein, and may also include a bulking agent, such as lactose, sorbitol, sucrose, or mannitol in amounts which facilitate dispersal of the powder from the device, e.g., 50 to 90% by weight of the formulation. The composition may be prepared in particulate form with an average particle size of less than 10 mm (or microns), most preferably 0.5 to 5 mm, for most effective delivery to the distal lung.

Nasal delivery of a pharmaceutical composition as discussed herein is also contemplated, for example, for treatment of allergic rhinitis (hay fever). Formulations for nasal delivery include those with dextran or cyclodextran. For nasal administration, a useful device is a small, hard bottle to which a metered dose sprayer is attached. In one embodiment, the metered dose is delivered by drawing a pharmaceutical composition into a chamber of defined volume, which chamber has an aperture dimensioned to aerosolize and aerosol formulation by forming a spray when a liquid in the chamber is compressed. The chamber may be compressed to administer the pharmaceutical composition of the present invention. In a specific embodiment, the chamber is a piston arrangement. Such devices are commercially available.

In another embodiment, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. In some cases, the nasal inhaler will provide a metered amount of the aerosol formulation, for administration of a measured dose of the drug.

Pharmaceutical formulations may include aqueous solutions of the compositions described herein in water-soluble form. Additionally, suspensions of the compositions may be prepared as appropriate oily injection suspensions. Suitable lipophilic solvents or vehicles include fatty oils such as sesame oil, or synthetic fatty acid esters, such as ethyl oleate or triglycerides, or liposomes. The suspensions may contain substances which alter the viscosity of the suspension, such as sodium carboxymethyl cellulose, sorbitol, or dextran. Optionally, the suspension may also contain suitable stabilizers or agents which increase the solubility of the compositions to allow for the preparation of highly concentrated solutions.

Alternatively, the active compositions may be in powder form for constitution with a suitable vehicle, e.g., sterile pyrogen-free water, before use.

In one set of embodiments, a composition such as is discussed herein may be applied to the skin of a subject, e.g., at any suitable location. The composition may be contacted using any suitable method. For example, the composition may be rubbed on, poured on, applied with an applicator (e.g., a gauze pad, a swab, a bandage, etc.), or the like. In some cases, the composition can be a liquid, a gel, a cream, a lotion, an ointment, a solid "stick," or the like, that can be applied to the skin or mucosal surface by hand, for example, by rubbing or spraying.

In some cases, the composition may be a topical preparation. Other components, for example, transdermal penetration enhancers, adjuvants, surfactants, lubricants, etc. can also be present in certain cases. Examples of transdermal penetration enhancers include, but are not limited to, 1,3-dimethyl-2-imidazolidinone or 1,2-propanediol. Other examples include cationic, anionic, or nonionic surfactants (e.g., sodium dodecyl sulfate, polyoxamers, etc.); fatty acids and alcohols (e.g., ethanol, oleic acid, lauric acid, liposomes, etc.); anticholinergic agents (e.g., benzilonium bromide, oxyphenonium bromide); alkanones (e.g., n-heptane); amides (e.g., urea, N,N-dimethyl-m-toluamide); organic acids (e.g., citric acid); sulfoxides (e.g., dimethylsulfoxide); terpenes (e.g., cyclohexene); ureas; sugars; carbohydrates or other agents. The transdermal penetration enhancers can be present in any suitable amount within the composition.

In addition to the formulations described previously, the compositions may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compositions, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems.

In certain embodiments of the invention, the administration of a composition may be designed so as to result in sequential exposures to the composition over a certain time period, for example, hours, days, weeks, months or years. This may be accomplished, for example, by repeated administrations of a composition of the invention by one of the methods described above, or by a sustained or controlled release delivery system in which the composition is delivered over a prolonged period without repeated administrations. Administration of the composition using such a delivery system may be, for example, by oral dosage forms, bolus injections, transdermal patches or subcutaneous implants. Maintaining a substantially constant concentration of the composition may be preferred in some cases.

Other delivery systems suitable for use with the present invention include time-release, delayed release, sustained release, or controlled release delivery systems. Such systems may avoid repeated administrations of the composition in many cases, increasing convenience to the subject. Many types of release delivery systems are available and known to those of ordinary skill in the art. They include, for example, polymer-based systems such as polylactic and/or polyglycolic acids, polyanhydrides, polycaprolactones and/or combinations of these; nonpolymer systems that are lipid-based including sterols such as cholesterol, cholesterol esters, and fatty acids or neutral fats such as mono-, di- and triglycerides; hydrogel release systems; liposome-based systems; phospholipid based-systems; silastic systems; peptide based systems; wax coatings; compressed tablets using conventional binders and excipients; or partially fused implants. Specific examples include, but are not limited to, erosional systems in which the composition is contained in a form within a matrix (for example, as described in U.S. Pat. Nos. 4,452,775, 4,675,189, and 5,736,152), or diffusional systems in which an active component controls the release rate (for example, as described in U.S. Pat. Nos. 3,854,480, 5,133,974 and 5,407,686). The formulation may be as, for example, microspheres, hydrogels, polymeric reservoirs, cholesterol matrices, or polymeric systems. In some embodiments, the system may allow sustained or controlled release of the composition to occur, for example, through control of the diffusion or erosion/degradation rate of the formulation containing the composition. In addition, a pump-based hardware delivery system may be used to deliver one or more embodiments of the invention.

Use of a long-term release implant may be particularly suitable in some embodiments of the invention. "Long-term release," as used herein, means that the implant containing the composition is constructed and arranged to deliver therapeutically effective levels of the composition for at least 30 or 45 days, and preferably at least 60 or 90 days, or even longer in some cases. Long-term release implants are well known to those of ordinary skill in the art, and include some of the release systems described above.

Administration of the composition can be alone, or in combination with other therapeutic agents and/or compositions. In certain embodiments of the invention, a composition can be combined with a suitable pharmaceutically acceptable carrier, for example, as incorporated into a liposome, incorporated into a polymer release system, or suspended in a liquid, e.g., in a dissolved form or a colloidal form. In general, pharmaceutically acceptable carriers suitable for use in the invention are well-known to those of ordinary skill in the art. As used herein, a "pharmaceutically acceptable carrier" refers to a non-toxic material that does not significantly interfere with the effectiveness of the biological activity of the active composition(s) to be administered, but is used as a formulation ingredient, for example, to stabilize or protect the active composition(s) within the composition before use. The carrier may include one or more compatible solid or liquid fillers, diluents or encapsulating substances which are suitable for administration to a human or other vertebrate animal. The term "carrier" denotes an organic or inorganic ingredient, which may be natural or synthetic, with which one or more compositions of the invention are combined to facilitate the application of the composition. The carrier may be co-mingled or otherwise mixed with one or more compositions of the present invention, and with each other, in a manner such that there is no interaction which would substantially impair the desired pharmaceutical efficacy. The carrier may be either soluble or insoluble, depending on the application. The nature of the carrier can be either soluble or insoluble. Those skilled in the art will know of other suitable carriers, or will be able to ascertain such, using only routine experimentation.

The formulations of the invention may be administered in pharmaceutically acceptable solutions, which may routinely contain pharmaceutically acceptable concentrations of salt, buffering agents, preservatives, compatible carriers, adjuvants, emulsifiers, diluents, excipients, chelating agents, fillers, drying agents, antioxidants, antimicrobials, preservatives, binding agents, bulking agents, silicas, solubilizers, stabilizers and optionally other therapeutic ingredients, that may be used with the active composition. For example, if the formulation is a liquid, the carrier may be a solvent, partial solvent, or non-solvent, and may be aqueous or organically based. Examples of suitable formulation ingredients include diluents such as calcium carbonate, sodium carbonate, lactose, kaolin, calcium phosphate, or sodium phosphate; granulating and disintegrating agents such as corn starch or algenic acid; binding agents such as starch, gelatin or acacia; lubricating agents such as magnesium stearate, stearic acid, or talc; time-delay materials such as glycerol monostearate or glycerol distearate; suspending agents such as sodium carboxymethylcellulose, methylcellulose, hydroxypropylmethylcellulose, sodium alginate, polyvinylpyrrolidone; dispersing or wetting agents such as lecithin or other naturally-occurring phosphatides; thickening agents such as cetyl alcohol or beeswax; buffering agents such as acetic acid and salts thereof, citric acid and salts thereof, boric acid and salts thereof, or phosphoric acid and salts thereof; or preservatives such as benzalkonium chloride, chlorobutanol, parabens, or thimerosal. Suitable carrier concentrations can be determined by those of ordinary skill in the art, using no more than routine experimentation. The compositions of the invention may be formulated into preparations in solid, semi-solid, liquid or gaseous forms such as tablets, capsules, elixirs, powders, granules, ointments, solutions, depositories, inhalants or injectables. Those of ordinary skill in the art will know of other suitable formulation ingredients, or will be able to ascertain such, using only routine experimentation.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Preparations include sterile aqueous or nonaqueous solutions, suspensions and emulsions, which can be isotonic with the blood of the subject in certain embodiments. Examples of nonaqueous solvents are polypropylene glycol, polyethylene glycol, vegetable oil such as olive oil, sesame oil, coconut oil, arachis oil, peanut oil, mineral oil, injectable organic esters such as ethyl oleate, or fixed oils including synthetic mono or di-glycerides. Aqueous carriers include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents and inert gases and the like. Those of skill in the art can readily determine the various parameters for preparing and formulating the compositions of the invention without resort to undue experimentation.

In some embodiments, the present invention includes the step of bringing a composition into association or contact with a suitable carrier, which may constitute one or more accessory ingredients. The final compositions may be prepared by any suitable technique, for example, by uniformly and intimately bringing the composition into association with a liquid carrier, a finely divided solid carrier or both, optionally with one or more formulation ingredients as previously described, and then, if necessary, shaping the product.

The compositions, and optionally other therapeutics, may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. The term "pharmaceutically acceptable salts" includes salts of the composition, prepared in combination with, for example, acids or bases, depending on the particular compositions found within the composition and the treatment modality desired. Pharmaceutically acceptable salts can be prepared as alkaline metal salts, such as lithium, sodium, or potassium salts; or as alkaline earth salts, such as beryllium, magnesium or calcium salts. Examples of suitable bases that may be used to form salts include ammonium, or mineral bases such as sodium hydroxide, lithium hydroxide, potassium hydroxide, calcium hydroxide, magnesium hydroxide, and the like. Examples of suitable acids that may be used to form salts include inorganic or mineral acids such as hydrochloric, hydrobromic, hydroiodic, hydrofluoric, nitric, carbonic, monohydrogencarbonic, phosphoric, monohydrogenphosphoric, dihydrogenphosphoric, sulfuric, monohydrogensulfuric, phosphorous acids and the like. Other suitable acids include organic acids, for example, acetic, propionic, isobutyric, maleic, malonic, benzoic, succinic, suberic, fumaric, mandelic, phthalic, benzenesulfonic, p-tolylsulfonic, citric, tartaric, methanesulfonic, glucuronic, galacturonic, salicylic, formic, naphthalene-2-sulfonic, and the like. Still other suitable acids include amino acids such as arginate, aspartate, glutamate, and the like. Also, such salts can be prepared as alkaline metal or alkaline earth salts, such as sodium, potassium or calcium salts of the carboxylic acid group.

In certain aspects, the present invention also provides any of the above-mentioned compositions in kits, optionally including instructions for use. That is, the kit can include a description of use of the composition for participation in any biological or chemical mechanism disclosed herein. The kits can further include a description of activity of the condition in treating the pathology, as opposed to the symptoms of the condition. That is, the kit can include a description of use of the compositions as discussed herein. The kit also can include instructions for use of a combination of two or more compositions of the invention, or instruction for use of a combination of a composition of the invention and one or more other compositions indicated for treatment of the oxidative stress condition. Instructions also may be provided for administering the composition by any suitable technique as previously described, for example, pulmonary or topical delivery.

The kits described herein may also contain one or more containers, which may contain the composition and other ingredients as previously described. The kits also may contain instructions for mixing, diluting, and/or administrating the compositions of the invention in some cases. The kits also can include other containers with one or more solvents, surfactants, preservative and/or diluents (e.g., normal saline (0.9% NaCl), or 5% dextrose) as well as containers for mixing, diluting or administering the components in a sample or to a subject in need of such treatment.

The compositions of the kit may be provided as any suitable form, for example, as liquid solutions or as dried powders. When the composition provided is a dry powder, the composition may be reconstituted by the addition of a suitable solvent, which may also be provided. In embodiments where liquid forms of the composition are used, the liquid form may be concentrated or ready to use. The solvent will depend on the composition and the mode of use or administration. Suitable solvents for drug compositions are well known, for example as previously described, and are available in the literature. The solvent will depend on the composition and the mode of use or administration.

U.S. Provisional Patent Application Ser. No. 62/245,114, filed Oct. 22, 2015, entitled "Inhibitors of Dual Oxidase 1 (DUOX1)," is incorporated herein by reference in its entirety.

The following examples are intended to illustrate certain embodiments of the present invention, but do not exemplify the full scope of the invention.

Example 1

This example is generally directed to electrophile-based inhibitors targeted to DUOX1 for treatment of allergic disorders.

The NADPH oxidase DUOX1 mediates certain features of allergic asthma. Allergic diseases are typically characterized by production of type 2 cytokines such as IL-4, IL-5 and IL-13, that are responsible for some important features of allergic asthma, such as eosinophilic inflammation, mucus metaplasia (contributing to airway obstruction), and airway remodeling leading to increased hyperresponsiveness and bronchoconstriction. Recent genome-wide association studies have identified a strong role for the cytokine IL-33 and its receptor (IL33R, ST2) in allergic diseases. IL-33 is a cytokine that is strongly expressed in epithelial cell in various barrier tissues, including lung and skin, and is rapidly released from epithelial cells in response to common asthma-inducing allergens, such as house dust mite (HDM) or fungal allergens, as well as other environmental triggers that may promote asthma development, such as ozone. Studies with cultured airway epithelial cells and in vivo studies in mice have shown that allergen-induced IL-33 secretion depends strongly on the NADPH oxidase DUOX1, which generates the oxidant $H_2O_2$ and thereby activates cell signaling pathways involving Src kinase and epidermal growth factor receptor (EGFR) by redox-dependent mechanisms. Expression of both IL-33 and DUOX1 are enhanced in the nasal epithelium from subjects with allergic asthma compared to healthy controls. Furthermore, EGFR is enhanced in the epithelium from asthmatics. Because DUOX1 appears to be an important mediator of both EGFR activation and IL-33 secretion in the airway epithelium, it is an appealing therapeutic target for preventing asthma symptoms that are associated with these events, such as exacerbations or bronchoconstriction.

Electrophilic compounds can suppress allergic inflammation and innate allergen responses. Animal exposure to non-toxic doses of acrolein (a well-known environmental pollutant and component of tobacco smoke) can dramatically suppress allergic inflammation and mucus metaplasia in a mouse model of allergic asthma. Acrolein exposure (at non-toxic doses) of mice can suppress acute airway responses to subsequent allergen challenge (HDM or the fungal allergen *Alternaria alternata*), shown by dramatically minimized production of IL-33, IL-1α or IL-17E (FIG. 1). This figure shows that acrolein inhalation suppresses innate airway responses to HDM. Mice were exposed to acrolein (5 ppm; 4 hrs, and subsequently challenged with HDM (50 micrograms), and BAL cytokines were analyzed 1 hour later.

These epithelia-derived cytokines have been demonstrated to contribute importantly to allergic asthma. Studies with cultured tracheal epithelial cells from mice or the human bronchial epithelial cell line HBE1, similarly showed that acrolein pretreatment inhibits allergen-induced secretion of IL-33, IL-1α or IL-17E in a dose-dependent manner (e.g. FIG. 2). In these examples, electrophiles inhibited HDM-induced IL-33 secretion from cultured mouse tracheal epithelial cells. Cells were pretreated with acrolein (ACR), cinnamaldehyde (CIN), curcumin (Curc) or sulforaphane (SFN) for 30 minutes and then stimulated with HDM for 2 hrs. IL-33 was measured in culture media.

Example 2

Based on identifying the involvement of $Ca^{2+}$-dependent DUOX1 activation and subsequent EGFR activation in allergen-induced IL-33 secretion from epithelial cells), the impact of acrolein exposure on allergen-induced $Ca^{2+}$ increases, extracellular $H_2O_2$ production (as a measure of DUOX1 activation) and EGFR tyrosine phosphorylation (as an indicator of EGFR activation) were studied. Results indicated that acrolein at non-toxic concentrations (3-30 micromolar) did not affect allergen-mediated $Ca^{2+}$ increases but markedly suppressed allergen-induced EGFR autophosphorylation as well as extracellular $H_2O_2$ production (FIG. 3).

Preliminary studies of DUOX1 targeting by electrophiles. Acrolein (2,3-propenal) is a highly reactive electrophile and a well-recognized environmental pollutant. In this example, other electrophilic compounds with similar chemical reactivity were determined to be capable of inhibiting allergen-induced DUOX1 activation. These studies were performed using immortalized human bronchoepithelial cells (HBE1) which were cultured and exposed to different electrophiles at various doses for 30 min prior to cell stimulation with HDM or with ATP (a known activator of DUOX1). Conditioned culture media was collected 10 min after cell stimulation and mixed for 15 min with 10 micrograms/mL lactoperoxidase (Sigma) and 1 mM tyrosine (Gibco), which results in formation of fluorescent dityrosine product as a function of $H_2O_2$ concentration, and was analyzed by HPLC with fluorescence detection and compared with exogenous standards based on similarly treated stock solutions of $H_2O_2$. The resulting data were corrected for basal $H_2O_2$ production by unstimulated cells and ATP-dependent $H_2O_2$ production in the presence of electrophiles were expressed relative to that by ATP alone (which was set at 100%).

These findings suggest that acrolein inhibits allergen-induced IL-33 production potentially by direct actions on DUOX1 at the epithelial surface. Although acrolein is a reactive electrophile that can induce cell stress by depleting cellular GSH (a major detoxicification mechanism for acrolein and other electrophiles), the inhibitory effects of acrolein on allergen-induced IL-33 secretion and $H_2O_2$ production occurred in the absence of cellular GSH depletion, suggesting a relatively selective mechanism. FIG. 3 shows acrolein pretreatment of HBE1 cells inhibits allergen-induced $H_2O_2$ production.

Several food-derived electrophiles that have been demonstrated to have anti-inflammatory activities were studied, such as curcumin ((1E,6E)-1,7-Bis(4-hydroxy-3-methoxyphenyl)-1,6-heptadiene-3,5-dione; from turmeric), sulforaphane (1-Isothiocyanato-4-methylsulfinylbutane; from cruciferous vegetables), or cinnamaldehyde ((2E)-3-phenylprop-2-enal; present in cinnamon), in a concentration range from 1-30 micromolar. Each of these compounds are known as "soft" electrophiles that selectively react with susceptible cysteine residues in proteins. Their anti-inflammatory actions have primarily been attributed to activation of Nrf2 and inhibition of NF-κB through direct reaction with cysteine residues of critical proteins involved in these pathways. It was found that each of these compounds was capable of inhibiting ATP-mediated $H_2O_2$ production (FIG. 4). Also studied was dimethylfumarate (DMF), an electrophile that is FDA-approved for treatment of multiple sclerosis (trade name Tecfidera), which also showed efficacy against psoriasis. DMF also may inhibit ATP-dependent $H_2O_2$ production. Inhibitory effects of phenyl vinyl sulfone, an electrophile that has formed the basis of several Cys-targeted covalent inhibitors was also shown. Collectively, these findings indicate that acrolein and other electrophiles are capable of inhibiting innate epithelial responses to allergens by targeting DUOX1 activation, and may thereby minimize allergen-induced allergic inflammation. These electrophiles may be able to suppress allergic inflammation in several diverse mouse models, and these results suggest that these inhibitory effects may at least partially be mediated by inhibition of DUOX1 activation.

FIG. 4 shows dose dependent inhibition of ATP-induced $H_2O_2$ production by HBE1 cells by various electrophiles. FIG. 4A shows dose-dependent inhibition by acrolein. FIG. 4B shows representative experiment showing dose-dependent inhibition by sulforaphane, cinnamaldehyde, dimethyl fumarate, or phenyl vinyl sulfonate. FIG. 4C shows relative inhibition by selected electrophiles (mean+/−S.D. from 3 experiments).

Since these various electrophiles act primarily by targeting susceptible cysteine residues by Michael addition, it was believed that they may directly target DUOX1 protein on one of its accessible cysteine residues within its extracellular peroxidase homology (PHD) domain. Reduced cysteine residues within this PHD domain may be essential for DUOX interactions with its maturation factors, which would suggest that selective targeting of these cysteines would interfere with such interactions and thus inhibit DUOX1 activity (see below). Moreover, since the PHD domain is unique to DUOX and not present in other NADPH oxidase isoforms, this targeting approach would avoid non-selective actions on these other isoforms, a common problem with most NADPH oxidase inhibitors currently in development. To determine whether acrolein-mediated inhibition of DUOX1 activity (FIG. 4) was associated with direct targeting of DUOX1 protein, HBE1 cells were treated with 0, 10, or 30 micromolar acrolein for 30 minutes and derivatized cell lysates with aldehyde reactive probe (ARP; Pierce), which converts acrolein-induced Michael adducts to induce a biotin tag. Biotin-tagged proteins were subsequently purified by avidin chromatography and collected biotin-tagged proteins (eluates) were then analyzed by 10% SDS-PAGE and western blotting with an alpha-DUOX1 antibody. Whole cell lysate were analyzed accordingly as loading controls. As shown in FIG. 5, acrolein treatment induced dose-dependent ARP labeling of DUOX1 (eluates blot) in HBE1 cells, whereas DUOX1 content in whole lysates remained constant. siRNA was used to silence DUOX1 prior to acrolein treatment to confirm that biotin labeling occurred on DUOX1, and the signal was indeed absent in DUOX1 siRNA targeted cells. This finding indicates that acrolein acts as an inhibitor of DUOX1 activity by formation of a direct adduct with DUOX1, putatively on Cys residue(s), and supports a strategy to develop electrophile-based inhibitors that are specifically targeted to DUOX1. FIG. 5 shows identification of DUOX1 targeting by acrolein using ARP labeling in HBE1 cells.

Example 3

Figure 6:
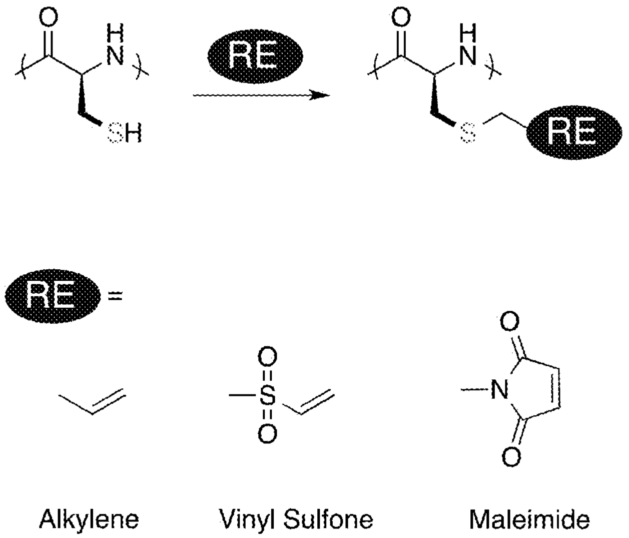
FIG. 6 illustrates certain reactive electrophiles in accordance with some embodiments of the invention.

Reactive Electrophiles (RE's) for Covalent Association to DUOX1. The design of covalently bonded or irreversible inhibitors is an attractive drug property for highly effective pharmaceuticals. Such covalent inhibitors have several advantages over non-covalent inhibitors, such as increased biochemical efficiency due to non-equilibrium binding, reduced sensitivity to pharmacokinetic parameters (e.g. clearance), and increased duration of action dependent on biological lifespan of the targeted protein. Reactive electrophiles (RE's) were studied in this example. RE's are known for their specific cysteine reactivity, and may include, for example, terminal alkylene, vinyl sulfone, and maleimide functional groups (FIG. 6). These RE-based targeting strategies are usually based on targeting a non-catalytic cysteine at or near an active site, although targeting of an extracellular cysteine in DUOX1 that is likely involved in DUOX1 maturation and activity (vide infra) may also be performed. FIG. 6 shows reactive electrophiles that can form covalent bonds with cysteine thiols in proteins.

The strategy to develop covalent inhibitors for DUOX1 would be to screen libraries of cysteine-reactive compounds for their ability to inhibit DUOX1 activation. However, protein-reactive compounds are usually avoided in high-throughput screening campaigns. Rational design of covalent inhibitors for DUOX1 is furthermore hindered by the fact that structural information of DUOX1 protein is largely lacking. A peptide-based approach was used, based on interactions between DUOX1 and DUOXA1 involving extracellular cysteines within the PHD domain of DUOX1. Since DUOX1 is primarily localized at the cell surface, such peptide-based targeting was facilitated due to high accessibility of targeted cysteines within the PHD domain without need of cellular entry or requirement for cell-penetrating peptides.

The DUOX1 inhibitor molecules may include short (n=5-9) polypeptide with a sequence informed by known protein-protein interactions, which directly affects the function of DUOX1, and/or incorporation of a cysteine-targeting electrophile capable of forming a covalent bond with DUOX1.

Functional DUOX1 depends on specific interactions with its maturation factor DUOXA1 (FIG. 7A). The conserved cysteine residues of the DUOX1 extracellular peroxidase homology domain (PHD) may maintain proper protein-protein interactions with its maturation factor DUOXA1. Moreover, structural modeling revealed that these cysteines are highly solvent exposed, suggesting that they are readily accessible for drug targeting. Another DUOX isoform, DUOX2, forms an intramolecular disulfide bridge with its maturation factor DUOXA2, which is essential for folding DUOX2 into an appropriate conformation in the endoplasmic reticulum and may be used in protein trafficking. It was expected that similar interactions govern the maturation and function of DUOX1 on the basis of high sequence homology between DUOX1 and DUOX2 (78%) and between DUOXA1 and DUOXA2 (58%) (FIG. 7B). Based on these findings, it is believed that short chain polypeptides inhibitors can be prepared based on the sequence of DUOXA1 that would selectively bind to DUOX1 and interfere with DUOX1-DUOXA1 interactions and thus inhibit DUOX1 activity.

Figures 10A, 10B, 10C:
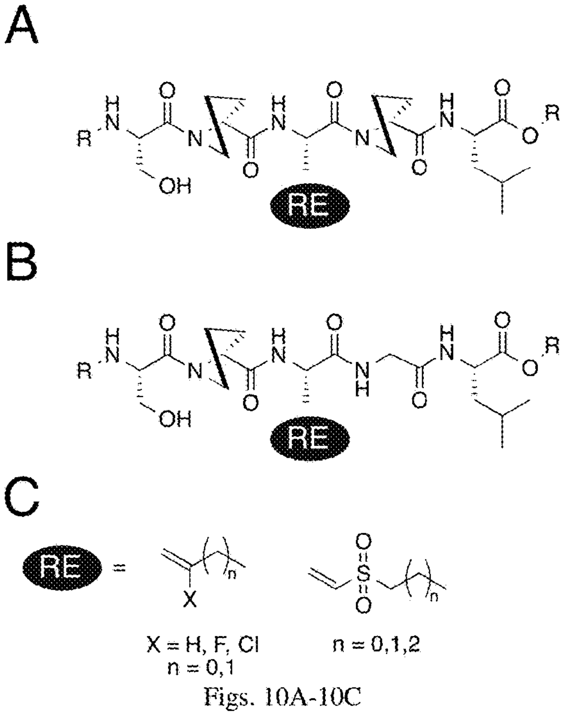
FIGS. 10A-10C illustrate some reactive electrophiles in accordance with some embodiments.

As illustrated in FIG. 10C, an inhibitor complex would have a short polypeptide modeled after the local sequence around conserved cysteines of DUOXA1 that are likely involved in interaction with DUOX1 (vide infra). This peptide would bind selectively as an affinity complex with DUOX1, likely via the extracellular domains, such as the PHD in FIG. 7. Importantly, since these cysteines are likely involved in intermolecular disulfide linking DUOX1 with DUOXA1, replacement of the cysteine position of these polypeptides with a modified amino acid containing a reactive electrophile (RE), illustrated in FIG. 10C, would increase efficacy and irreversibility due to covalent targeting of DUOX1. FIG. 7 shows design of covalent drugs for the inhibition of DUOX1 on the foundation of its native interactions with DUOXA1 and containing a reactive electrophile (RE) to form the covalent bond to DUOX1.

DUOX1 may form a protein-protein interaction including an intermolecular disulfide with DUOX1A, tuhs, the sequences include cysteine residues. Examination of the DUOXA1 sequence aligned with respect to DUOXA2 revealed two conserved cysteine residues, C167 and C234 (FIGS. 7A and 8A), that are both located within the extracellular domains of DUOXA1 and assessable for binding to the PHD of DUOX1. Notably, amino acid sequences around these cysteine residues are conserved and constitute an SPCXL (SEQ ID NO: 35) motif, which was a starting point for building peptide-based affinity scaffolds (FIGS. 8B and 8C). Moreover, both are proximal to proline residues, which are unique residues with structural rigidity and may provide directed orientation of these cysteines for efficient disulfide bond formation, which may efficiently direct RE's toward forming covalent bonds with the inhibitor molecules. Taken together, the surrounding sequences of C167 and C234 that facilitate productive, disulfide mediated binding of DUOXA1 in order to properly mature DUOX1 will provide building blocks for selective polypeptides for inhibition of DUOX1 activity. FIG. 8 shows sequence similarity of cysteine flanking residues in the DUOXA1 protein. FIG. 8A shows BLAST sequence alignment of DUOXA1 and DUOXA2. FIG. 8B shows a comparison of the DUOXA1 sequences for Cys167 and Cys234. FIG. 8C shows a sequence of small chain peptide containing cysteine on the basis of DUOXA1 residues. X indicates a different amino acid in the sequence.

Peptide Synthesis. Conventional solid-state polypeptide synthesis (SSPS) can be used for producing peptide-based drugs that will allow for the incorporation non-natural amino acids, namely those including cysteine-targeting RE's, for the production of specific irreversible inhibitors. To produce a given peptide, the residue at the "C-terminus" will start bound to resin and reacted with the second amino acid containing a protected amine, e.g., fluorenylmethyloxycarbonyl (Fmoc). This will continue until the ideal polypeptide (n=5-9) is obtained. All naturally occurring L-amino acids are commercially available including N-protected Fmoc groups.

Figure 9:
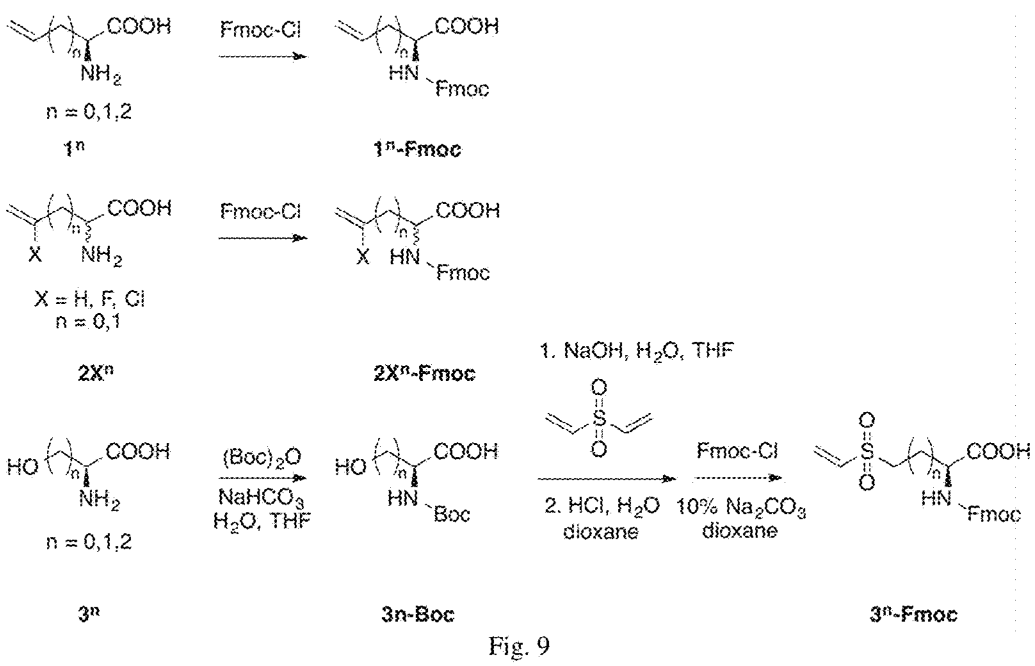
FIG. 9 illustrates synthesis of certain reactive electrophiles, in accordance with certain embodiments of the invention.

Incorporation of the RE into the SSPS-derived peptides will require synthesis, as these are not commercially available. From available starting materials, synthesis of reactive electrophile of SSPS compatible amino acid-like building blocks to produce inhibitors is shown in FIG. 9. Acrolein-like terminal alkyl vinyl compounds that can be obtained commercially and feature variable alkyl lengths (n=0,1,2; FIG. 9, top and middle). Beta-halide derivatives (2″F and 2″Cl) are available in racemic (R and S) enantiomers while alkyl compounds 1″ can be purchased as S enantiomers. These amino acids can be made compatible with SSPS via reaction with Fmoc-Cl in dioxane (1″-Fmoc and 2″X-Fmoc). Preparation of a vinyl sulfone amino acid, a reactive electrophile reported to target cysteine residues pharamacologically and shown to inhibit DUOX1 activity (vide supra) can also be readily synthesized from available starting materials. Primary alcohol amino acids (3″) can be functionalized with vinyl sulfone functional groups via the reaction with divinyl sulfone under basic conditions (FIG. 9, bottom). This requires initial protection of the amine, which can be performed prior to this addition with standard N-Boc protection. The Boc group will be deprotected upon acid workup of the addition product with divinyl sulfone. Fmoc-Cl reprotection of the resulting deprotected amine will produce SSPS compatible vinyl sulfone amino acid building blocks. FIG. 9 shows synthesis of SSPS compatible reactive electrophiles containing variable lengths of terminal vinyl groups with β-functionalization and vinyl sulfones.

Incorporation of these reactive electrophiles (1″-Fmoc, 2″X-Fmoc, 3″-Fmoc) in the same sequence as the C167 and C234 will allow irreversible, covalent bond forming reactivity in peptides derived from DUOXA1. Bringing together the sequences the reactive electrophiles in FIG. 9 allow for a variety of compounds, including peptides of n=5 length with sequences S-P-RE-G-L (SEQ ID NO: 33) or S-P-RE-P-L (SEQ ID NO: 34) (where RE represents the position of the reactive electrophiles (RE)). These two peptides are the closest in sequence to C167 and C234 in DUOXA1, respectively, and represent "minimal" peptide models.

Examples of peptide compounds will be designed consisting of the conserved S-P-RE-G/P-L (SEQ ID NO: 8) motif as shown in FIG. 10. FIGS. 10A and 10B show two SSPS-derived molecules readily synthesizable from available starting materials (see above). RE's from FIG. 9 can be incorporated into these compounds. FIG. 10 shows selective inhibitors consisting of minimal polypeptide length based on sequence identity of Cys167 and Cys234 of DUOXA1. Polypeptide synthetic products for DUOX1 inhibitors based on sequences flanking (FIG. 10A) Cys167 and (FIG. 10B) Cys234 of DUOXA1 that may selectively bind DUOX1. Note that R═H for simplest products and can be modified after peptide synthesis. FIG. 10C shows reactive electrophiles synthesized from available starting materials (see FIG. 9) that can be included in the middle of the peptides in FIGS. 10A and 10B.

Reasonable lengths of SSPS-derived polypeptides include those with nine amino acid residue. Longer variants of these peptides featured in FIGS. 10A and 10B are also possible. Including the S-P-RE-G/P-L (SEQ ID NO: 8) sequence as constant, combinations of peptide include, but are not limited to: R/T-S-P-RE-G/P-L (n=6) (SEQ ID NO: 14), P/L-R/T-S-P-RE-G/P-L (n=7) (SEQ ID NO: 19), T/S-P/L-R/T-S-P-RE-G/P-L (n=8) (SEQ ID NO: 24), F/T-T/S-P/L-R/T-S-P-RE-G/P-L (n=9) (SEQ ID NO: 29), S-P-RE-G/P-L-Y/H (n=6) (SEQ ID NO: 10), S-P-RE-G/P-L-Y/H-R/L (n=7) (SEQ ID NO: 11), S-P-RE-G/P-L-Y/H-R/L-Q/G (n=8) (SEQ ID NO: 12), S-P-RE-G/P-L-Y/H-R/L-Q/G-Y/A (n=9) (SEQ ID NO: 13) R/T-S-P-RE-G/P-L-Y/H (n=7) (SEQ ID NO: 15), R/T-S-P-RE-G/P-L-Y/H-R/L (n=8) (SEQ ID NO: 16), and R/T-S-P-RE-G/P-L-Y/H-R/L-Q/G (n=9) (SEQ ID NO: 17), etc. Note that when an amino acid is varied once in a peptide, it represents two different peptides in these examples. If an amino acid is varied twice in a peptide, it represents four different peptides and so on.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles “a” and “an,” as used herein in the specification and in the claims, unless clearly indicated to the contrary, should be understood to mean “at least one.”

The phrase “and/or,” as used herein in the specification and in the claims, should be understood to mean “either or both” of the elements so conjoined, i.e., elements that are conjunctively present in some cases and disjunctively present in other cases. Multiple elements listed with “and/or” should be construed in the same fashion, i.e., “one or more” of the elements so conjoined. Other elements may optionally be present other than the elements specifically identified by the “and/or” clause, whether related or unrelated to those elements specifically identified. Thus, as a non-limiting example, a reference to “A and/or B”, when used in conjunction with open-ended language such as “comprising” can refer, in one embodiment, to A only (optionally including elements other than B); in another embodiment, to B only (optionally including elements other than A); in yet another embodiment, to both A and B (optionally including other elements); etc.

As used herein in the specification and in the claims, “or” should be understood to have the same meaning as “and/or” as defined above. For example, when separating items in a list, “or” or “and/or” shall be interpreted as being inclusive, i.e., the inclusion of at least one, but also including more than one, of a number or list of elements, and, optionally, additional unlisted items. Only terms clearly indicated to the contrary, such as “only one of” or “exactly one of,” or, when used in the claims, “consisting of,” will refer to the inclusion of exactly one element of a number or list of elements. In general, the term “or” as used herein shall only be interpreted as indicating exclusive alternatives (i.e. “one or the other but not both”) when preceded by terms of exclusivity, such as “either,” “one of,” “only one of,” or “exactly one of.” “Consisting essentially of,” when used in the claims, shall have its ordinary meaning as used in the field of patent law.

As used herein in the specification and in the claims, the phrase “at least one,” in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase “at least one” refers, whether related or unrelated to those elements specifically identified. Thus, as a non-limiting example, “at least one of A and B” (or, equivalently, “at least one of A or B,” or, equivalently “at least one of A and/or B”) can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the word “about” is used herein in reference to a number, it should be understood that still another embodiment of the invention includes that number not modified by the presence of the word “about.”

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as “comprising,” “including,” “carrying,” “having,” “containing,” “involving,” “holding,” “composed of,” and the like are to be understood to be open-ended, i.e., to mean including but not limited to. Only the transitional phrases “consisting of” and “consisting essentially of” shall be closed or semi-closed transitional phrases, respectively, as set forth in the United States Patent Office Manual of Patent Examining Procedures, Section 2111.03.

What is claimed is:

1. A composition, comprising:

a peptide comprising a sequence:

S-P-Re-J-L, (SEQ ID NO: 8)

wherein Re is a reactive electrophile and J is G or P.

2. The composition of claim 1, wherein Re is able to covalently bind to a cysteine.

3. The composition of claim 1, wherein Re is able to covalently bind to a cysteine within DUOX1.

4. The composition of claim 1, wherein Re is able to covalently bind to a cysteine within the peroxidase homology domain of DUOX1.

5. The composition of claim 1, wherein Re comprises an alkylene moiety.

6. The composition of claim 1, wherein Re has a side chain having a structure:

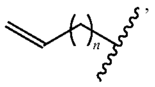

wherein n is 0, 1, or 2.

7. The composition of claim 1, wherein Re has a side chain having a structure:

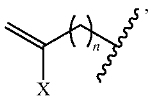

wherein X is H, F, or Cl, and n is 0, 1, or 2.

8. The composition of claim 1, wherein Re comprises a vinyl sulfone moiety.

9. The composition of claim 1, wherein Re has a side chain having a structure:

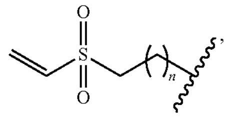

wherein n is 0, 1, or 2.

10. The composition of claim 1, wherein Re has a side chain having a structure:

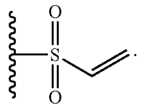 [SMILES: *S(=O)(=O)C=C]

11. The composition of claim 1, wherein Re comprises a maleimide moiety.

12. The composition of claim 1, wherein the peptide has no more than 9 amino acid residues.

13. The composition of claim 1, wherein the composition comprises a particle comprising the peptide.

14. The composition of claim 13, wherein the particle has a mass median aerodynamic diameter of no more than about 10 micrometers.

15. The composition of claim 1, wherein the composition is contained within an inhaler.

16. A method, comprising:

administering, to a subject, a composition comprising a peptide comprising a sequence:

S-P-Re-J-L, (SEQ ID NO: 8)

wherein Re is a reactive electrophile and J is G or P.

17. The method of claim 16, wherein the composition is an aerosol.

18. The method of claim 16, wherein the subject has or is at risk for an allergic disease.

19. The method of claim 16, comprising administering the composition to a lung of the subject.

20. The method of claim 16, wherein the subject has or is at risk for asthma.

* * * * *